US012077772B2

(12) United States Patent
Gray et al.

(10) Patent No.: US 12,077,772 B2
(45) Date of Patent: Sep. 3, 2024

(54) TRANSGENE CASSETTES, AAV VECTORS AND AAV VIRAL VECTORS FOR THE EXPRESSION OF HUMAN CODON-OPTIMIZED SLC6A1

(71) Applicant: THE BOARD OF REGENTS OF THE UNIVERSITY OF TEXAS SYSTEM, Austin, TX (US)

(72) Inventors: Steven J. Gray, Southlake, TX (US); Frances C. Shaffo, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 348 days.

(21) Appl. No.: 17/092,240

(22) Filed: Nov. 7, 2020

(65) Prior Publication Data

US 2021/0139934 A1 May 13, 2021

Related U.S. Application Data

(60) Provisional application No. 62/932,824, filed on Nov. 8, 2019.

(51) Int. Cl.

| | |
|---|---|
| ***C12N 15/86*** | (2006.01) |
| ***A61K 9/00*** | (2006.01) |
| ***A61K 38/17*** | (2006.01) |
| ***A61K 48/00*** | (2006.01) |
| ***C07K 14/705*** | (2006.01) |
| ***C12N 7/00*** | (2006.01) |

(52) U.S. Cl.

CPC ............ *C12N 15/86* (2013.01); *A61K 9/0085* (2013.01); *A61K 38/1787* (2013.01); *A61K 48/005* (2013.01); *A61K 48/0083* (2013.01); *C07K 14/70571* (2013.01); *C12N 7/00* (2013.01); *C12N 2750/14143* (2013.01); *C12N 2800/22* (2013.01); *C12N 2830/50* (2013.01)

(58) Field of Classification Search

CPC ..................... C12N 15/86; C12N 7/00; C12N 2750/14143; C12N 2800/22; C12N 2830/50; C12N 2830/008; C12N 2830/15; A61K 9/0085; A61K 38/1787; A61K 48/005; A61K 48/0083; A61K 48/0075; A61K 9/5184; A01K 2217/075; A01K 2227/105; A01K 2267/0356; C07K 14/70571; C07K 14/47

See application file for complete search history.

(56) References Cited

U.S. PATENT DOCUMENTS

2008/0213765 A1* 9/2008 Philippi .................. A61P 25/22 435/7.1
2011/0129831 A1 6/2011 Cargill et al.
2021/0170051 A1* 6/2021 Gray .................. C07K 14/4703

FOREIGN PATENT DOCUMENTS

WO 2006090288 A2 8/2006

OTHER PUBLICATIONS

Maertens et al. "Gene optimization mechanisms: a multi-gene study reveals a high success rate of full-length human proteins expressed in *Escherichia coli*." Protein Science 19.7 (2010): 1312-1326 (Year: 2010).*

Naso et al. "Adeno-associated virus (AAV) as a vector for gene therapy." BioDrugs 31.4 (2017): 317-334 (Year: 2017).*

PCT International Application No. PCT/US20/59576, International Search Report of the International Searching Authority, dated Feb. 19, 2021, 5 pages.

PCT International Application No. PCT/US20/59576, Written Opinion of the International Searching Authority, dated Feb. 19, 2021, 8 pages.

Ling et al, "Enhanced Transgene Expression from Recombinant Single-stranded D-Sequence-Substituted Adeno- Associated Virus Vectors in Human Cell Lines In Vitro and in Murine Hepatocytes in Vivo", Journal of Virology, vol. 89, No. 2, pp. 952-961, Jan. 2015.

Ozlu et al, "Gene Transfer Therapy for Neurodevelopment Disorders", Dev Neurosci, vol. 43, pp. 230-240, Apr. 21, 2021.

Extended European Search Report issued in EP Application No. 20884323, 6 pages, dated Dec. 4, 2023.

* cited by examiner

*Primary Examiner* — Jeremy C Flinders
*Assistant Examiner* — Alexander W Nicol
(74) *Attorney, Agent, or Firm* — DLA Piper LLP US

(57) ABSTRACT

The present disclosure provides methods and compositions for the treatment of diseases and genetic disorders linked to SLC6A1 loss and/or misfunction. The methods and compositions of the present disclosure comprise rAAV vectors and rAAV viral vectors comprising transgene nucleic acid molecules comprising nucleic acid sequences encoding for a GAT1 polypeptide.

21 Claims, 8 Drawing Sheets

Specification includes a Sequence Listing.

| Modified AAV2 ITR | *Promoter Sequence | Transgene nucleic acid molecule comprising a codon-optimized nucleic acid sequencing encoding a GAT1 polyptpide | SV40 polyA sequence | AAV2 ITR |
|---|---|---|---|---|

5'　　　　　　　　　　　　　　　　　　　　　　　　　　　　　　3'

*Either JET or MeP229 promoter

TRANSGENE CASSETTES, AAV VECTORS AND AAV VIRAL VECTORS FOR THE EXPRESSION OF HUMAN CODON-OPTIMIZED SLC6A1

CROSS REFERENCE TO RELATED APPLICATIONS

This application claims priority to U.S. Provisional Application Nos. 62/932,824, filed Nov. 8, 2019, the contents of which are incorporated by reference herein in its entirety for all purposes.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Nov. 7, 2020, is named "426871-000171_ST25(003).txt" and is about 58.9 KB in size.

BACKGROUND

SLC6A1 is a gene that encodes for GABA transporter 1 (GAT1, also known as solute carrier family 6 member 1 or sodium- and chloride-dependent GABA transporter 1) in human subjects. GAT1 is a gamma-aminobutyric acid (GABA) transporter which removes GABA from the synaptic cleft. GAT1 uses the energy from the dissipation of the sodium gradient, aided by the presence of a chloride gradient, to translocate GABA across the membranes of neurons in the central nervous systems. Loss-of-function mutations in SLC6A1 have been linked to a variety of different neurological conditions with symptoms including seizures, epilepsy and intellectual disability. Specifically, SLC6A1 haploinsufficiency is a rare neurological disease in which a patient lacks one copy of a functional SLC6A1 gene. Thus, there is a need in the art for compositions and methods for gene therapy for diseases and genetic disorders linked to SLC6A1 loss and/or misfunction.

SUMMARY

The present disclosure relates generally to the field of gene therapy and in particular, to recombinant adeno-associated viral (AAV) vector particles (also known as rAAV viral vectors) comprising transgene sequences encoding for GAT1 polypeptides, their manufacture, and their use to deliver transgenes to treat or prevent a disease or disorder, including diseases associated with loss and/or misfunction of the SLC6A1 gene.

The present disclosure provides a recombinant adeno-associated virus (rAAV) vector comprising in 5' to 3' direction: (a) a first AAV inverted terminal repeat (ITR) sequence; (b) a promoter sequence; (c) a transgene nucleic acid molecule, wherein the transgene nucleic acid molecule comprises a nucleic acid sequence encoding for a GAT1 polypeptide; (d) a polyA sequence; and (e) a second AAV ITR sequence.

A GAT1 polypeptide can comprise the amino acid sequence set forth in SEQ ID NO: 1.

A nucleic acid sequence encoding for a GAT1 polypeptide can be a codon optimized nucleic acid sequence encoding for a GAT1 polypeptide. A codon optimized nucleic acid sequence encoding for a GAT1 polypeptide can comprise the nucleic acid sequence set forth in SEQ ID NO: 3. A codon optimized nucleic acid sequence encoding for a GAT1 polypeptide can comprise the nucleic acid sequence set forth in SEQ ID NO: 6. A codon optimized nucleic acid sequence encoding for a GAT1 polypeptide can exhibit at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence.

A first AAV ITR sequence can comprise the nucleic acid sequence set forth in SEQ ID NO: 12. A second AAV ITR sequence can comprise the nucleic acid sequence set forth in SEQ ID NO: 13.

A promoter sequence can comprise a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, EF1a promoter, Ubc promoter, human β-actin promoter, TRE promoter, Ac5 promoter, Polyhedrin promoter, CaMKIIa promoter, Gal1 promoter, TEF1 promoter, GDS promoter, ADH1 promoter, Ubi promoter, or α-1-antitrypsin (hAAT) promoter. A promoter sequence can comprise the nucleic acid sequence set forth in SEQ ID NO: 14. A promoter sequence can comprise the nucleic acid sequence set forth in SEQ ID NO: 15.

A polyA sequence can comprise the nucleic acid sequence set forth in SEQ ID NO: 16.

The present disclosure provides an rAAV vector comprising, in the 5' to 3' direction: a) a first AAV ITR sequence comprising the nucleic acid sequence set forth in SEQ ID NO: 12; b) a promoter sequence comprising the nucleic acid sequence set forth in SEQ ID NO: 14; c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence set forth in SEQ ID NO: 3; d) a polyA sequence comprising the nucleic acid sequence set forth in SEQ ID NO: 16; and e) a second AAV ITR sequence comprising the nucleic acid sequence set forth in SEQ ID NO: 13.

The present disclosure provides an rAAV vector of any one of the preceding claims, comprising, in the 5' to 3' direction: a) a first AAV ITR sequence comprising the nucleic acid sequence set forth in SEQ ID NO: 12; b) a promoter sequence comprising the nucleic acid sequence set forth in SEQ ID NO: 15; c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence set forth in SEQ ID NO: 3; d) a polyA sequence comprising the nucleic acid sequence set forth in SEQ ID NO: 16; and e) a second AAV ITR sequence comprising the nucleic acid sequence set forth in SEQ ID NO: 13.

An rAAV vector can comprise the nucleic acid sequence set forth in SEQ ID NO: 20.

An rAAV vector can comprise the nucleic acid sequence set forth in SEQ ID NO: 22.

The present disclosure provides an rAAV viral vector comprising: (i) an AAV capsid protein; and (ii) an rAAV vector of the present disclosure An AAV capsid protein can be an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein. An AAV capsid protein can be an AAV9 capsid protein.

The present disclosure provides a pharmaceutical composition comprising: a) a rAAV viral vector of the present disclosure; and at least one pharmaceutically acceptable excipient and/or additive.

The present disclosure provides a method for treating a subject having a disease and/or disorder involving a SLC6A1 gene, the method comprising administering to the subject at least one therapeutically effective amount of the rAAV viral vector or pharmaceutical composition of the present disclosure The present disclosure provides an rAAV viral vector or pharmaceutical composition of the present disclosure for use in treating a disease and/or disorder involving a SLC6A1 gene in a subject in need thereof.

A disease and/or disorder involving the SLC6A1 gene can be SLC6A1 haploinsufficiency or Doose Syndrome.

An rAAV viral vector or pharmaceutical composition of the present disclosure can be administered to the subject at a dose ranging from about $10^{11}$ to about $10^{18}$ viral vector particles.

An rAAV viral vector or pharmaceutical composition of the present disclosure can be administered to the subject at a dose ranging from about $10^{13}$ to about $10^{16}$ viral vector particles.

An rAAV viral vector or pharmaceutical composition of the present disclosure can be administered to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. An rAAV viral vector or pharmaceutical composition of the present disclosure can be administered intrathecally.

Any of the above aspects, or any other aspect described herein, can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION

Figure 1:
FIG. 1 is a representative image of RNAscope analysis of five micron paraffin-embedded sagittal sections of brains from mice that were intrathecally administered an rAAV viral vector of the present disclosure comprising a transgene nucleic acid molecule comprising a SLC6A1 nucleic acid sequence.

The present disclosure provides, inter alia, isolated polynucleotides, recombinant adeno-associated virus (rAAV) vectors, and rAAV viral vectors comprising transgene nucleic acid molecules comprising nucleic acid sequences encoding for GAT1 polypeptides. The present disclosure also provides methods of manufacturing these isolated polynucleotides, rAAV vectors, and rAAV viral vectors, as well as their use to deliver transgenes to treat or prevent a disease or disorder, including diseases associated with loss and/or misfunction of an SLC6A1 gene.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3: 1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types. At least 11 sequentially numbered AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAV PHP.B. The AAV particle comprises, consists essentially of, or consists of three major viral proteins: VP1, VP2 and VP3. In some aspects, the AAV refers to the serotype AAV1, AAV2, AAV4, AAV5, AAV6, AAV7, AAV8, AAV9, AAV10, AAV11, AAV12, AAV13, AAVPHP.B, AAVrh74 or AAVrh.10.

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10, AAV11, AAV12, AAV13, AAVPHP.B, AAVrh74 and AAVrh.10). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (described in detail in Kerun et al. JCI Insight, 2019; 4(22):e131610) and AAV-NP59 (described in detail in Paulk et al. Molecular Therapy, 2018; 26(1): 289-303).

AAV Structure and Function

AAV is a replication-deficient parvovirus, the single-stranded DNA genome of which is about 4.7 kb in length, including two 145-nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928. U.S. Pat. No. 9,434,928 also provides the sequences of the capsid proteins and a self-complementary genome. In one aspect, an AAV genome is a self-complementary genome. Cis-acting sequences directing viral DNA replication (rep), encapsidation/packaging, and host cell chromosome integration are contained within AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome.

The cap gene is expressed from the p40 promoter and encodes the three capsid proteins, VP1, VP2, and VP3. Alternative splicing and non-consensus translational start sites are responsible for the production of the three related capsid proteins. More specifically, after the single mRNA from which each of the VP1, VP2 and VP3 proteins are translated is transcribed, it can be spliced in two different manners: either a longer or shorter intron can be excised, resulting in the formation of two pools of mRNAs: a 2.3 kb- and a 2.6 kb-long mRNA pool. The longer intron is often preferred and thus the 2.3-kb-long mRNA can be called the major splice variant. This form lacks the first AUG codon, from which the synthesis of VP1 protein starts, resulting in a reduced overall level of VP1 protein synthesis. The first AUG codon that remains in the major splice variant is the initiation codon for the VP3 protein. However, upstream of that codon in the same open reading frame lies an ACG sequence (encoding threonine) which is surrounded by an optimal Kozak (translation initiation) context. This contributes to a low level of synthesis of the VP2 protein, which is actually the VP3 protein with additional N terminal residues, as is VP1, as described in Becerra S P et al., (December 1985). "Direct mapping of adeno-associated virus capsid proteins B and C: a possible ACG initiation codon". Proceedings of the National Academy of Sciences of the United States of America. 82 (23): 7919-23, Cassinotti P et al., (November 1988). "Organization of the adeno-associated virus (AAV) capsid gene: mapping of a minor spliced mRNA coding for virus capsid protein 1". Virology. 167 (1): 176-84, Muralidhar S et al., (January 1994). "Site-directed mutagenesis of adeno-associated virus type 2 structural protein initiation codons: effects on regulation of synthesis and biological activity". Journal of Virology. 68 (1): 170-6, and Trempe J P, Carter B J (September 1988). "Alternate mRNA splicing is required for synthesis of adeno-associated virus VP1 capsid protein". Journal of Virology. 62 (9): 3356-63, each of which is herein incorporated by reference. A single consensus polyA site is located at map position 95 of the AAV genome. The life cycle and genetics of AAV are reviewed in Muzyczka, Current Topics in Microbiology and Immunology, 158: 97-129 (1992).

Each VP1 protein contains a VP1 portion, a VP2 portion and a VP3 portion. The VP1 portion is the N-terminal portion of the VP1 protein that is unique to the VP1 protein. The VP2 portion is the amino acid sequence present within the VP1 protein that is also found in the N-terminal portion of the VP2 protein. The VP3 portion and the VP3 protein have the same sequence. The VP3 portion is the C-terminal portion of the VP1 protein that is shared with the VP1 and VP2 proteins.

The VP3 protein can be further divided into discrete variable surface regions I-IX (VR-I-IX). Each of the variable surface regions (VRs) can comprise or contain specific amino acid sequences that either alone or in combination with the specific amino acid sequences of each of the other VRs can confer unique infection phenotypes (e.g., decreased antigenicity, improved transduction and/or tissue-specific tropism relative to other AAV serotypes) to a particular serotype as described in DiMatta et al., "Structural Insight into the Unique Properties of Adeno-Associated Virus Serotype 9" J. Virol., Vol. 86 (12): 6947-6958, June 2012, the contents of which are incorporated herein by reference.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA to generate AAV vectors. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes of the invention comprise, consist essentially of, or consist of a nucleic acid molecule encoding a therapeutic protein (e.g., GAT1) and one or more AAV ITRs flanking the nucleic acid molecule. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

Isolated Polynucleotides Comprising Transgene Sequences

The present disclosure provides isolated polynucleotides comprising at least one transgene nucleic acid molecule.

In some aspects, a transgene nucleic acid molecule can comprise a nucleic acid sequence encoding a GAT1 polypeptide, or at least one fragment thereof. As would be appreciated by the skilled artisan, GAT1 is encoded for by the SLC6A1 gene in the human genome. Thus, a transgene nucleic acid molecule can comprise, consist essentially of, or consist of an SLC6A1 sequence, or any fragment thereof. In some aspects, a transgene nucleic acid molecule can comprise a nucleic acid sequence encoding a biological equivalent of a GAT1 polypeptide.

In some aspects, a GAT1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence put forth in SEQ ID NO: 1 or SEQ ID NO: 2, or a fragment thereof. In some aspects, a GAT1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to at least one portion of the amino acid sequence put forth in SEQ ID NO: 1, or a fragment thereof.

In some aspects, a nucleic acid sequence encoding a GAT1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to any one of the nucleic acid sequences put forth in SEQ ID NOs: 3-10. In some aspects, a nucleic acid sequence encoding a GAT1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NOs: 6. A nucleic acid sequence encoding a GAT1 polypeptide can be referred to as a SLC6A1 sequence.

In some aspects, the nucleic acid sequence encoding a GAT1 polypeptide can be a codon optimized nucleic acid sequence that encodes for a GAT1 polypeptide. A codon optimized nucleic acid sequence encoding a GAT1 polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the GAT1 polypeptide. As used herein, the "wildtype human nucleic acid sequence encoding the GAT1 polypeptide" refers to the nucleic acid sequence that encodes the GAT1 polypeptide in a human genome, as put forth in SEQ ID NO: 11.

SEQ ID NOs: 3-10 are unique codon optimized nucleic acid sequences that encode for a GAT1 polypeptide.

In some aspects, a codon optimized nucleic acid sequence encoding a GAT1 polypeptide, such as those put forth in SEQ ID NOs: 3-10, can comprise no donor splice sites. In some aspects, a codon optimized nucleic acid sequence encoding a GAT1 polypeptide can comprise no more than about one, or about two, or about three, or about four, or about five, or about six, or about seven, or about eight, or about nine, or about ten donor splice sites. In some aspects, a codon optimized nucleic acid sequence encoding a GAT1 polypeptide comprises at least one, or at least two, or at least three, or at least four, or at least five, or at least six, or at least seven, or at least eight, or at least nine, or at least ten fewer donor splice sites as compared to the wildtype human nucleic acid sequence encoding the GAT1 polypeptide. Without wishing to be bound by theory, the removal of donor splice sites in the codon optimized nucleic acid sequence can unexpectedly and unpredictably increase expression of the GAT1 polypeptide in vivo, as cryptic splicing is prevented. Moreover, cryptic splicing may vary between different subjects, meaning that the expression level of the GAT1 polypeptide comprising donor splice sites may unpredictably vary between different subjects. Such unpredictability is unacceptable in the context of human therapy. Accordingly, the codon optimized nucleic acid sequence, such as those put forth in SEQ ID NOs: 3-10, which lacks donor splice sites, unexpectedly and surprisingly allows for increased expression of the GAT1 polypeptide in human subjects and regularizes expression of the GAT1 polypeptide across different human subjects.

In some aspects, a codon optimized nucleic acid sequence encoding a GAT1 polypeptide, such as those put forth in SEQ ID NOs: 3-10, can have a GC content that differs from the GC content of the wildtype human nucleic acid sequence encoding the GAT1 polypeptide. In some aspects, the GC content of a codon optimized nucleic acid sequence encoding a GAT1 polypeptide is more evenly distributed across the entire nucleic acid sequence, as compared to the wildtype human nucleic acid sequence encoding the GAT1 polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

In some aspects, a codon optimized nucleic acid sequence encoding a GAT1 polypeptide, such as those put forth in SEQ ID NOs: 3-10, can have fewer repressive microRNA target binding sites as compared to the wildtype human nucleic acid sequence encoding the GAT1 polypeptide. In some aspects, a codon optimized nucleic acid sequence encoding a GAT1 polypeptide can have at least one, or at least two, or at least three, or at least four, or at least five, or at least six, or at least seven, or at least eight, or at least nine, or at least ten, or at least ten fewer repressive microRNA target binding sites as compared to the wildtype human nucleic acid sequence encoding the GAT1 polypeptide. Without wishing to be bound by theory, by having fewer repressive microRNA target binding sites, the codon optimized nucleic acid sequence encoding a GAT1 polypeptide unexpectedly exhibits increased expression in a human subject.

In some aspects, the codon optimized nucleic acid sequence encoding a GAT1 polypeptide exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding a GAT1 polypeptide.

AAV Vectors

In some aspects, the isolated polynucleotides comprising at least one transgene nucleic acid molecule described herein can be a recombinant AAV (rAAV) vector.

As used herein, the term "vector" refers to a nucleic acid comprising, consisting essentially of, or consisting of an intact replicon such that the vector may be replicated when placed within a cell, for example by a process of transfection, infection, or transformation. It is understood in the art that once inside a cell, a vector may replicate as an extra-chromosomal (episomal) element or may be integrated into a host cell chromosome. Vectors may include nucleic acids derived from retroviruses, adenoviruses, herpesvirus, baculoviruses, modified baculoviruses, papovaviruses, or otherwise modified naturally-occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, consisting essentially of, or consisting of DNA condensed with cationic polymers such as heterogeneous polylysine, defined-length oligopeptides, and polyethyleneimine, in some cases contained in liposomes; and the use of ternary complexes comprising, consisting essentially of, or consisting of a virus and polylysine-DNA.

With respect to general recombinant techniques, vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif) and Promega Biotech (Madison, Wis.). In order to optimize expression and/or in vitro transcription, it may be necessary to remove, add or alter 5' and/or 3' untranslated portions of cloned transgenes to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

An "rAAV vector" as used herein refers to a vector comprising, consisting essentially of, or consisting of one or more transgene sequences and one or more AAV inverted terminal repeat sequences (ITRs). Such AAV vectors can be replicated and packaged into infectious viral particles when present in a host cell that provides the functionality of rep and cap gene products; for example, by transfection of the host cell. In some aspects, AAV vectors contain a promoter, at least one nucleic acid that may encode at least one protein or RNA, and/or an enhancer and/or a terminator within the flanking ITRs that is packaged into the infectious AAV particle. The encapsidated nucleic acid portion may be referred to as the AAV vector genome. Plasmids containing rAAV vectors may also contain elements for manufacturing purposes, e.g., antibiotic resistance genes, origin of replication sequences etc., but these are not encapsidated and thus do not form part of the AAV particle.

In some aspects, an rAAV vector can comprise at least one transgene nucleic acid molecule. In some aspects, an rAAV vector can comprise at least one AAV inverted terminal (ITR) sequence. In some aspects, an rAAV vector can comprise at least one promoter sequence. In some aspects, an rAAV vector can comprise at least one enhancer sequence. In some aspects, an rAAV vector can comprise at least one polyA sequence. In some aspects, an rAAV vector can comprise at least one reporter protein.

In some aspects, an rAAV vector can comprise a first AAV ITR sequence, a promoter sequence, a transgene nucleic acid molecule, a polyA sequence, and a second AAV ITR sequence. In some aspects, an rAAV vector can comprise, in the 5' to 3' direction, a first AAV ITR sequence, a promoter sequence, a transgene nucleic acid molecule, a polyA sequence, and a second AAV ITR sequence.

In some aspects, an rAAV vector can comprise more than one transgene nucleic acid molecule. In some aspects, an rAAV vector can comprise at least two transgene nucleic acid molecules, such that the rAAV vector comprises a first transgene nucleic acid molecule and an at least second transgene nucleic acid molecule. In some aspects, the first and the at least second transgene nucleic acid molecule can comprise the same nucleic acid sequence. In some aspects, the first and the at least second transgene nucleic acid molecules can comprise different nucleic acid sequences. In some aspects, the first and the at least second transgene nucleic acid sequences can be adjacent to each other.

In some aspects, an rAAV vector can comprise more than one promoter sequence. In some aspects, an rAAV vector can comprise at least two promoter sequences, such that the rAAV vector comprises a first promoter sequence and an at least second promoter sequence. In some aspects, the first and the at least second promoter sequences can comprise the same sequence. In some aspects, the first and the at least second promoter sequences can comprise different sequences. In some aspects, the first and the at least second promoter sequences can be adjacent to each other. In some aspects wherein an rAAV vector also comprises a first transgene nucleic acid molecule and an at least second transgene nucleic acid molecule, the first promoter can be located upstream (5') of the first transgene nucleic acid molecule and the at least second promoter can be located between the first transgene nucleic acid molecule and the at least second transgene nucleic acid molecule, such that the at least second promoter is downstream (3') of the first transgene nucleic acid molecule and upstream (5') of the at least second transgene nucleic acid molecule.

Any of the preceding rAAV vectors can further comprise at least one enhancer. The at least one enhancer can be located anywhere in the rAAV vector. In some aspects, the at least one enhancer can be located immediately upstream (5') of a promoter. Thus, an rAAV vector can comprise, in the 5' to 3' direction, a first AAV ITR sequence, an enhancer, a promoter sequence, a transgene nucleic acid molecule, a polyA sequence, and a second AAV ITR sequence. In some aspects, the at least one enhancer can be located immediately downstream (3') of a promoter. Thus, an rAAV vector can comprise, in the 5' to 3' direction, a first AAV ITR sequence, a promoter sequence, an enhancer, a transgene nucleic acid molecule, a polyA sequence, and a second AAV ITR sequence. In some aspects, the at least one enhancer can be located immediately downstream of a transgene nucleic acid molecule. Thus, an rAAV vector can comprise, in the 5' to 3' direction, a first AAV ITR sequence, a promoter sequence, a transgene nucleic acid molecule, an enhancer, a polyA sequence, and a second AAV ITR sequence.

AAV ITR Sequences

In some aspects, an AAV ITR sequence can comprise any AAV ITR sequence known in the art. In some aspects, an AAV ITR sequence can be an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence or an AAVrh.10 ITR sequence.

Thus, in some aspects, an AAV ITR sequence can comprise, consist essentially of, or consist of an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, or an AAVrh.10 ITR sequence.

In some aspects, an rAAV vector of the present disclosure can comprise, consist essentially of, or consist of AAV2 ITR sequences. In some aspects, an rAAV vector of the present disclosure can comprise, consist essentially of, or consist of AAV2 ITR sequences or a modified AAV2 ITR sequence.

In some aspects, an AAV2 ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13.

In some aspects, a modified AAV2 ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12.

Promoter Sequence and Enhancers

The term "promoter" and "promoter sequence" as used herein means a control sequence that is a region of a polynucleotide sequence at which the initiation and rate of transcription of a coding sequence, such as a gene or a transgene, are controlled. Promoters may be constitutive, inducible, repressible, or tissue-specific, for example. Promoters may contain genetic elements at which regulatory proteins and molecules such as RNA polymerase and transcription factors may bind. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, an H1 promoter, a ubiquitous chicken β-actin hybrid (CBh) promoter, a small nuclear RNA (U1a or U1b) promoter, an MeCP2 promoter, an MeP418 promoter, an MeP426 promoter, a minimal MeCP2 promoter, a VMD2 promoter, an mRho promoter, or an EF1 promoter.

Additional non-limiting exemplary promoters provided herein include, but are not limited to EF1a, Ubc, human β-actin, CAG, TRE, Ac5, Polyhedrin, CaMKIIa, Gal1, TEF1, GDS, ADH1, Ubi, and α-1-antitrypsin (hAAT). It is known in the art that the nucleotide sequences of such promoters may be modified in order to increase or decrease the efficiency of mRNA transcription. See, e.g., Gao et al. (2018) Mol. Ther.: Nucleic Acids 12:135-145 (modifying TATA box of 7SK, U6 and H1 promoters to abolish RNA polymerase III transcription and stimulate RNA polymerase II-dependent mRNA transcription). Synthetically-derived promoters may be used for ubiquitous or tissue specific expression. Further, virus-derived promoters, some of which are noted above, may be useful in the methods disclosed herein, e.g., CMV, HIV, adenovirus, and AAV promoters. In some aspects, the promoter is used together with at least one enhancer to increase the transcription efficiency. Non-limiting examples of enhancers include an interstitial retinoid-binding protein (IRBP) enhancer, an RSV enhancer or a CMV enhancer.

In some aspects, a promoter sequence can comprise, consist essentially of, or consist of a Rous sarcoma virus (RSV) LTR promoter sequence (optionally with the RSV enhancer), a cytomegalovirus (CMV) promoter sequence, an SV40 promoter sequence, a dihydrofolate reductase promoter sequence, a β-actin promoter sequence, a phosphoglycerol kinase (PGK) promoter sequence, a U6 promoter sequence, an H1 promoter sequence, a ubiquitous chicken β-actin hybrid (CBh) promoter sequence, a small nuclear RNA (U1a or U1b) promoter sequence, an MeCP2 promoter sequence, an MeP418 promoter sequence, an MeP426 promoter sequence, a minimal MeCP2 promoter sequence, a VMD2 promoter sequence, an mRho promoter sequence, an EFI promoter sequence, an EF1a promoter sequence, a Ubc promoter sequence, a human β-actin promoter sequence, a CAG promoter sequence, a TRE promoter sequence, an Ac5 promoter sequence, a Polyhedrin promoter sequence, a CaMKIIa promoter sequence, a Gal1 promoter sequence, a TEF1 promoter sequence, a GDS promoter sequence, an ADH1 promoter sequence, a Ubi promoter sequence or an α-1-antitrypsin (hAAT) promoter sequence.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) or synthetic techniques such that transcription of that gene is directed by the linked enhancer/promoter. Non-limiting examples of linked enhancer/promoter for use in the methods, compositions and constructs provided herein include a PDE promoter plus IRBP enhancer or a CMV enhancer plus U1a promoter. It is understood in the art that enhancers can operate from a distance and irrespective of their orientation relative to the location of an endogenous or heterologous promoter. It is thus further understood that an enhancer operating at a distance from a promoter is thus "operably linked" to that promoter irrespective of its location in the vector or its orientation relative to the location of the promoter.

As used throughout the disclosure, the term "operably linked" refers to the expression of a gene (i.e. a transgene) that is under the control of a promoter with which it is spatially connected. A promoter can be positioned 5' (upstream) or 3' (downstream) of a gene under its control. A promoter can be positioned 5'(upstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

In some aspects, a promoter sequence can comprise, consist essentially of, or consist of a JeT promoter sequence. A JeT promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 14.

In some aspects, a promoter sequence can comprise, consist essentially of, or consist of a MeP229 promoter sequence. A meP229 promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 14.

In some aspects, a promoter sequence can comprise, consist essentially of, or consist of a CBh promoter sequence. A CBh promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 24.

In some aspects, bacterial plasmids of the present disclosure can comprise a prokaryotic promoter.

A prokaryotic promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 19.

Transgene Nucleic Acid Molecules

In some aspects, a transgene nucleic acid molecule can comprise a nucleic acid sequence encoding a GAT1 polypeptide, or at least one fragment thereof. In some aspects, a transgene nucleic acid molecule can comprise a nucleic acid sequence encoding a biological equivalent of a GAT1 polypeptide, or at least one fragment thereof.

In some aspects, a GAT1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence put forth in SEQ ID NO: 1 or SEQ ID NO: 2, or a fragment thereof. In some aspects, a GAT1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to at least one portion of the amino acid sequence put forth in SEQ ID NO: 1, or a fragment thereof.

In some aspects, a nucleic acid sequence encoding a GAT1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to any one of the nucleic acid sequences put forth in SEQ ID NOs: 3-10. In some aspects, a nucleic acid sequence encoding a GAT1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NOs: 6. A nucleic acid sequence encoding a GAT1 polypeptide can be referred to as a SLC6A1 sequence.

In some aspects, a nucleic acid sequence encoding a GAT1 polypeptide can be a codon optimized nucleic acid sequence that encodes for a GAT1 polypeptide. A codon optimized nucleic acid sequence encoding a GAT1 polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the GAT1 polypeptide. As used herein, the "wildtype human nucleic acid sequence encoding the GAT1 polypeptide" refers to the nucleic acid sequence that encodes the GAT1 polypeptide in a human genome, as set forth in, for example, SEQ ID NO: 11.

SEQ ID NOs: 3-10 are unique codon optimized nucleic acid sequences that encode for a GAT1 polypeptide.

In some aspects, a transgene nucleic acid molecule can comprise, consist essentially of, or consist of a nucleic acid sequence encoding a reporter protein. As used herein, a reporter protein is a detectable protein that is operably linked to a promoter to assay the expression (for example, tissue specificity and/or strength) of the promoter. In aspects, a reporter protein may be operably linked to a polypeptide. In aspects, reporter proteins may be used in monitoring DNA delivery methods, functional identification and characterization of promoter and enhancer elements, translation and transcription regulation, mRNA processing and protein: protein interactions. Non-limiting examples of a reporter protein are β-galactosidase; a fluorescent protein, such as, Green Fluorescent Protein (GFP) or Red Fluorescent Protein (RFP); luciferase; glutathione S-transferase; and maltose binding protein.

In some aspects, a transgene nucleic acid molecule can further comprise a nucleic acid sequence encoding a signal peptide.

In some aspects, a transgene nucleic acid molecule present in an rAAV vector can be under transcriptional control of a promoter sequence also present in the same rAAV vector.

polyA Sequences

In some aspects, a polyadenylation (polyA) sequence can comprise any polyA sequence known in the art. Non-limiting examples of polyA sequences include, but are not limited to, an MeCP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

Thus, a polyA sequence can comprise, consist essentially of, or consist of an MeCP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

In some aspects, a polyA sequence can comprise, consist essentially of, or consist of an SV40pA sequence. In some aspects, an SV40pA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 16.

Bacterial Plasmids

In some aspects, the rAAV vectors of the present disclosure can be contained within a bacterial plasmid to allow for propagation of the rAAV vector in vitro. Thus, the present disclosure provides bacterial plasmids comprising any of the rAAV vectors described herein. A bacterial plasmid can further comprise an origin of replication sequence. A bacterial plasmid can further comprise an antibiotic resistance gene. A bacterial plasmid can further comprise a prokaryotic promoter.

Figure 6:
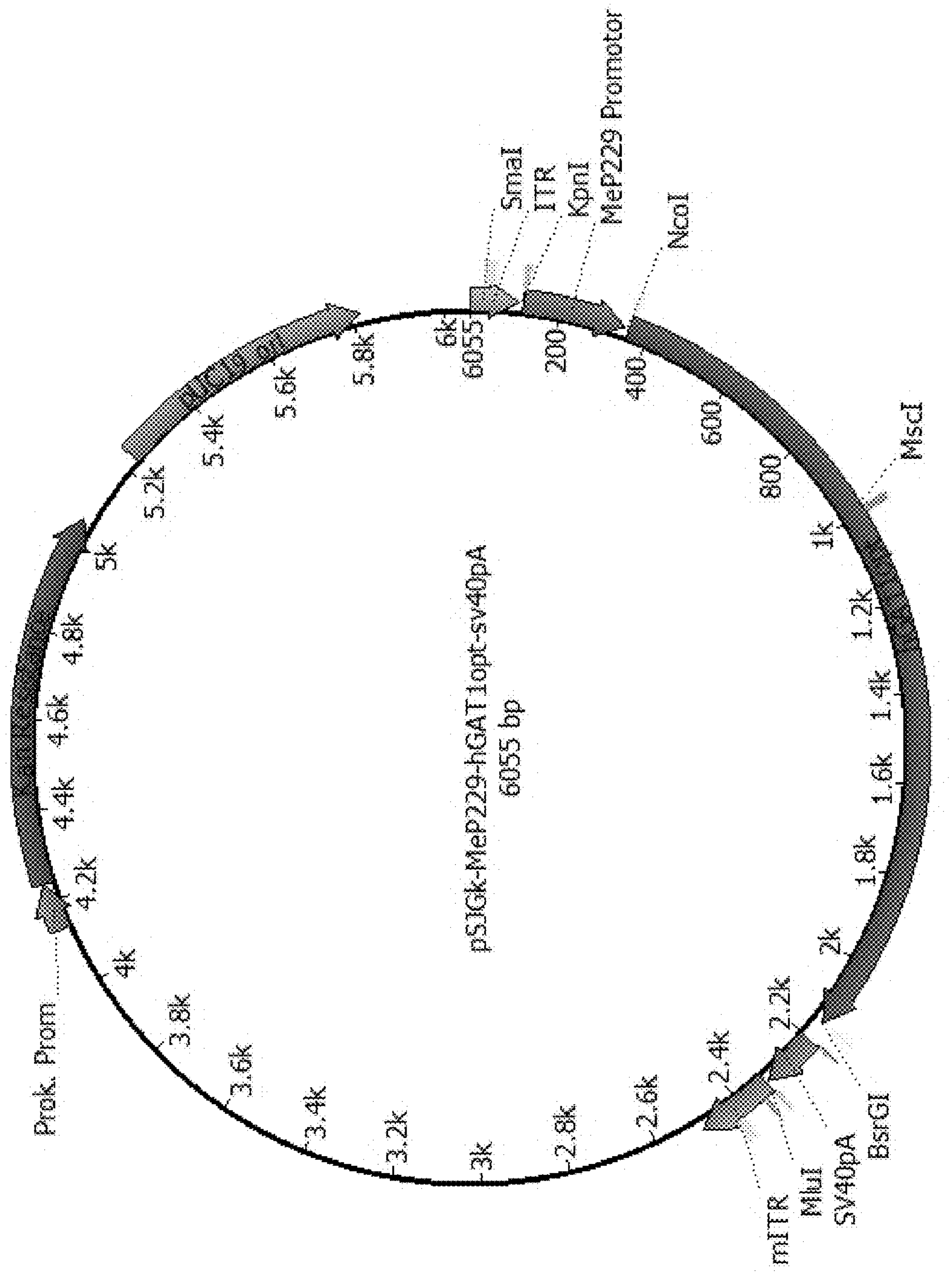
FIG. 6 is a an exemplary schematic of a bacterial plasmid comprising an rAAV vector, wherein the rAAV vector in the bacterial plasmid comprises, in the 5' to 3' direction, a modified AAV2 ITR, a MeP229 promoter sequence, a transgene nucleic acid molecule comprising a codon-optimized nucleic acid sequence encoding a GAT1 polypeptide, an SV40pA sequence and an AAV2 ITR.

An exemplary schematic of a bacterial plasmid comprising an rAAV vector is shown in FIG. 6. In this non-limiting example, the rAAV vector in the bacterial plasmid comprises, in the 5' to 3' direction, a modified AAV2 ITR, a JeT promoter sequence, a transgene nucleic acid molecule comprising a codon-optimized nucleic acid sequence encoding a GAT1 polypeptide, an SV40pA sequence and an AAV2 ITR.

Figure 7:
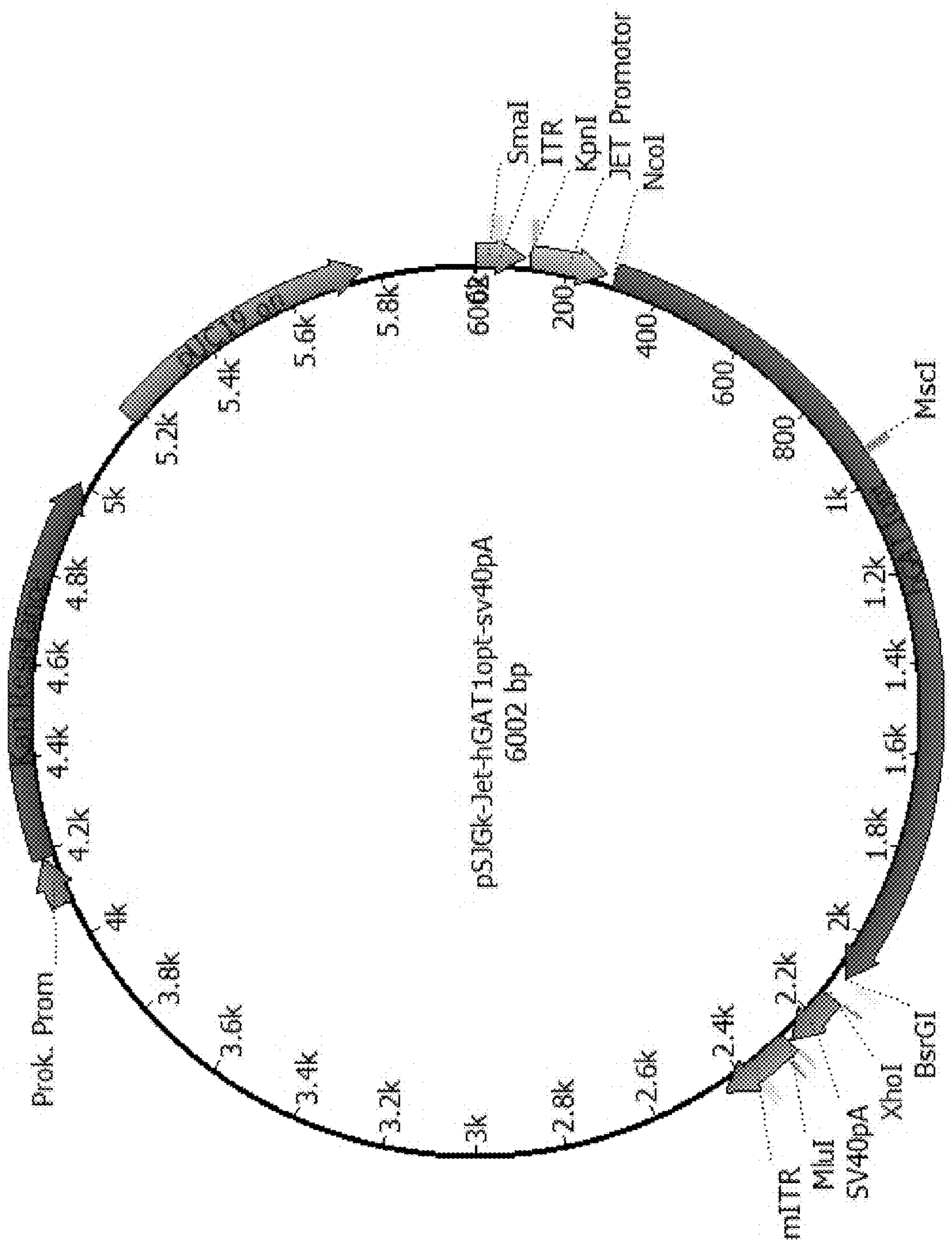
FIG. 7 is an exemplary schematic of a bacterial plasmid comprising an rAAV vector, wherein the rAAV vector in the bacterial plasmid comprises, in the 5' to 3' direction, a modified AAV2 ITR, a MeP229 promoter sequence, a transgene nucleic acid molecule comprising a codon-optimized nucleic acid sequence encoding a GAT1 polypeptide, an SV40pA sequence and an AAV2 ITR.
Figure 8:
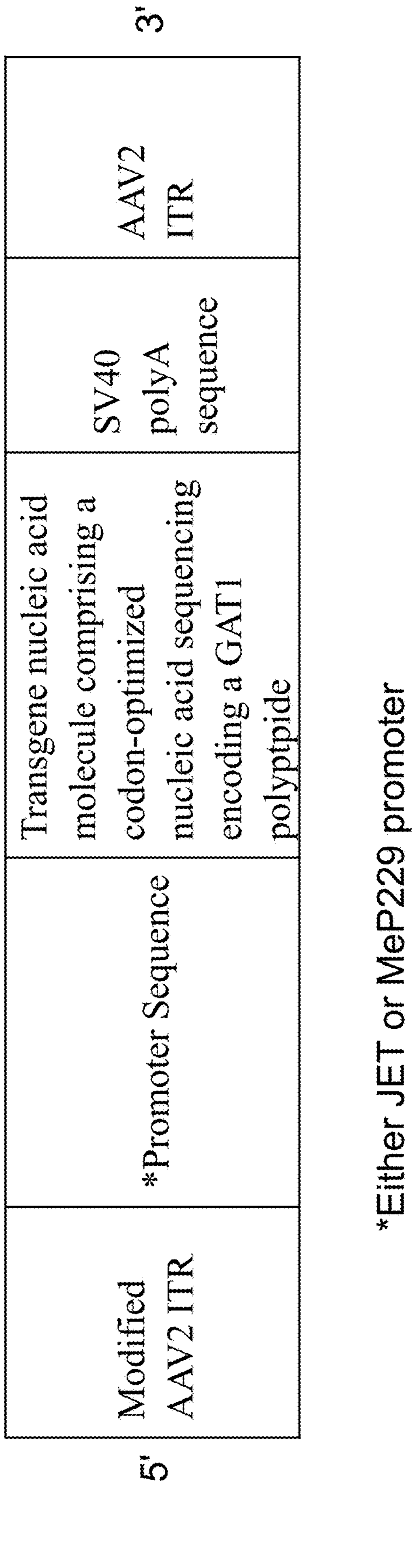
FIG. 8 is an exemplary schematic of an rAAV vector of the present disclosure, wherein the rAAV vector comprises in the 5' to 3' direction, a modified AAV2 ITR, either a JeT promoter sequence or a meP229 promoter sequence, a transgene nucleic acid molecule comprising a codon-optimized nucleic acid sequence encoding a GAT1 polypeptide, an SV40pA sequence and an AAV2 ITR.

An exemplary schematic of a bacterial plasmid comprising an rAAV vector is shown in FIG. 7. In this non-limiting example, the rAAV vector in the bacterial plasmid comprises, in the 5' to 3' direction, a modified AAV2 ITR, a JeT promoter sequence, a transgene nucleic acid molecule comprising a codon-optimized nucleic acid sequence encoding a GAT1 polypeptide, an SV40pA sequence and an AAV2 ITR.

In some aspects, a bacterial plasmid of the present disclosure can comprise, consist essentially of, or consist of the nucleic acid sequence set forth in SEQ ID NO: 21.

In some aspects, a bacterial plasmid of the present disclosure can comprise, consist essentially of, or consist of the nucleic acid sequence set forth in SEQ ID NO: 23.

Origin of Replication Sequence

In some aspects, an origin of replication sequence can comprise, consist essentially of, or consist of any origin of replication sequence known in the art. The origin of replication sequence can be a bacterial origin of replication sequence, thereby allowing the rAAV vector comprising said bacterial origin of replication sequence to be produced, propagated and maintained in bacteria, using methods standard in the art.

In some aspects, an origin of replication sequence can comprise, consist essentially of, or consist of a pUC19 origin of replication sequence. A pUC19 origin of replication sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 17.

Antibiotic Resistance Genes

In some aspects, rAAV vectors and/or rAAV viral vectors of the disclosure can comprise an antibiotic resistance gene.

In some aspects, an antibiotic resistance gene can comprise, consist essentially of, or consist of any antibiotic resistance genes known in the art. Examples of antibiotic resistance genes known in the art include, but are not limited to kanamycin resistance genes, spectinomycin resistance genes, streptomycin resistance genes, ampicillin resistance genes, carbenicillin resistance genes, bleomycin resistance genes, erythromycin resistance genes, polymyxin B resistance genes, tetracycline resistance genes and chloramphenicol resistance genes.

In some aspects, an antibiotic resistance gene can comprise, consist essentially of, or consist of a kanamycin antibiotic resistance gene. A kanamycin antibiotic resistance gene can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 18.

AAV Viral Vectors

A "viral vector" is defined as a recombinantly produced virus or viral particle that contains a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, e.g., Schlesinger and Dubensky (1999) Curr. Opin. Biotechnol. 5:434-439 and Ying, et al. (1999) Nat. Med. 5(7):823-827.

An "AAV virion" or "AAV viral particle" or "AAV viral vector" or "rAAV viral vector" or "AAV vector particle" or "AAV particle" refers to a viral particle composed of at least one AAV capsid protein and an encapsidated polynucleotide rAAV vector. Thus, production of an rAAV viral vector necessarily includes production of an rAAV vector, as such a vector is contained within an rAAV vector.

As used herein, the term "viral capsid" or "capsid" refers to the proteinaceous shell or coat of a viral particle. Capsids function to encapsidate, protect, transport, and release into the host cell a viral genome. Capsids are generally comprised of oligomeric structural subunits of protein ("capsid proteins"). As used herein, the term "encapsidated" means enclosed within a viral capsid. The viral capsid of AAV is composed of a mixture of three viral capsid proteins: VP1, VP2, and VP3. The mixture of VP1, VP2 and VP3 contains 60 monomers that are arranged in a T=1 icosahedral symmetry in a ratio of 1:1:10 (VP1:VP2:VP3) or 1:1:20 (VP1:VP2:VP3) as described in Sonntag F et al., (June 2010). "A viral assembly factor promotes AAV2 capsid formation in the nucleolus". Proceedings of the National Academy of Sciences of the United States of America. 107 (22): 10220-5, and Rabinowitz J E, Samulski R J (December 2000). "Building a better vector: the manipulation of AAV virions". Virology. 278 (2): 301-8, each of which is incorporated herein by reference in its entirety.

The present disclosure provides an rAAV viral vector comprising: a) any of the rAAV vectors described herein; and b) an AAV capsid protein.

An AAV capsid protein can be any AAV capsid protein known in the art. An AAV capsid protein can be an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

Alternative rAAV Vectors and rAAV Viral Vectors Embodiments

The present disclosure provides the following embodiments:

1. An rAAV vector, comprising, in the 5' to 3' direction
   a) a first AAV ITR sequence;
   b) a promoter sequence;
   c) a transgene nucleic acid molecule, wherein the transgene nucleic acid molecule comprises a nucleic acid sequence encoding for a GAT1 polypeptide;
   d) a polyA sequence; and
   e) a second AAV ITR sequence.
2. The rAAV vector of embodiment 1, wherein the nucleic acid sequence encoding for a GAT1 polypeptide is a codon optimized nucleic acid sequence.
3. The rAAV vector of embodiment 1 or embodiment 2, wherein the GAT1 polypeptide comprises the amino acid sequence of SEQ ID NO: 1 or SEQ ID NO: 2.
4. The rAAV vector of embodiment 3, wherein the GAT1 polypeptide comprises the amino acid sequence of SEQ ID NO: 1.
5. The rAAV vector of embodiment 3, wherein the GAT1 polypeptide comprises the amino acid sequence of SEQ ID NO: 2.
6. The rAAV vector of any one of the preceding embodiments, wherein the codon optimized transgene sequence eliminates a predicted donor splice site.
7. The rAAV vector of any one of the preceding embodiments, wherein the codon optimized transgene sequence has a higher GC content than the wild-type transgene sequence.
8. The rAAV vector of any one of the preceding embodiments, wherein the GC content of the codon optimized transgene sequence is more evenly distributed across the entire nucleic acid sequence as compared to the wild-type transgene sequence.
9. The rAAV vector of any one of the preceding embodiments, wherein the nucleic acid sequence encoding for a GAT1 polypeptide comprises any one of the nucleic acid sequences set forth in SEQ ID NOs: 3-10.
10. The rAAV vector of embodiment 9, wherein the nucleic acid sequence encoding for a GAT1 polypeptide comprises the nucleic acid sequence of SEQ ID NO: 3.
11. The rAAV vector of embodiment 9, wherein the nucleic acid sequence encoding for a GAT1 polypeptide comprises the nucleic acid sequence of SEQ ID NO: 4.
12. The rAAV vector of embodiment 9, wherein the nucleic acid sequence encoding for a GAT1 polypeptide comprises the nucleic acid sequence of SEQ ID NO: 5.
13. The rAAV vector of embodiment 9, wherein the nucleic acid sequence encoding for a GAT1 polypeptide comprises the nucleic acid sequence of SEQ ID NO: 6.
14. The rAAV vector of embodiment 9, wherein the nucleic acid sequence encoding for a GAT1 polypeptide comprises the nucleic acid sequence of SEQ ID NO: 7.
15. The rAAV vector of embodiment 9, wherein the nucleic acid sequence encoding for a GAT1 polypeptide comprises the nucleic acid sequence of SEQ ID NO: 8.
16. The rAAV vector of embodiment 9, wherein the nucleic acid sequence encoding for a GAT1 polypeptide comprises the nucleic acid sequence of SEQ ID NO: 9.
17. The rAAV vector of embodiment 9, wherein the nucleic acid sequence encoding for a GAT1 polypeptide comprises the nucleic acid sequence of SEQ ID NO: 10.
18. The rAAV vector of any one of the preceding embodiments, wherein the first AAV ITR sequence is a modified AAV2 ITR sequence.

19. The rAAV vector of any one of the preceding embodiments, wherein the first AAV ITR sequence comprises the nucleic acid sequence of SEQ ID NO: 12.

20. The rAAV vector of any one of the preceding embodiments, wherein the second AAV ITR sequence is an AAV2 ITR sequence.

21. The rAAV vector of any one of the preceding embodiments, wherein the second AAV ITR sequence comprises the nucleic acid sequence of SEQ ID NO: 13.

22. The rAAV vector of any one of the preceding embodiments, wherein the promoter sequence comprises a JeT promoter sequence.

23. The rAAV vector of embodiment 22, wherein the JeT promoter sequence comprises the nucleic acid sequence of SEQ ID NO: 14.

24. The rAAV vector of any one of the preceding embodiments, wherein the promoter sequence comprises a MeP229 promoter sequence.

25. The rAAV vector of embodiment 24, wherein the MeP229 promoter sequence comprises the nucleic acid sequence of SEQ ID NO: 15.

26. The rAAV vector of any one of the preceding embodiments, wherein the polyA sequence comprises an SV40pA sequence.

27. The rAAV vector of embodiment 26, wherein the SV40pA sequence comprises the nucleic acid sequence of SEQ ID NO: 16.

28. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 14;

c) a transgene nucleic acid molecule, wherein the transgene nucleic acid molecule comprises a nucleic acid sequence encoding for a GAT1 polypeptide, wherein the GAT1 polypeptide comprises the amino acid sequence of SEQ ID NO: 1 or SEQ ID NO: 2;

d) a polyA sequence comprising the nucleic acid sequence of SEQ ID NO: 16; and e) a second AAV ITR sequence comprising the nucleic acid sequence of SEQ ID NO: 13.

29. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 15;

c) a transgene nucleic acid molecule, wherein the transgene nucleic acid molecule comprises a nucleic acid sequence encoding for a GAT1 polypeptide, wherein the GAT1 polypeptide comprises the amino acid sequence of SEQ ID NO: 1 or SEQ ID NO: 2;

d) a polyA sequence comprising the nucleic acid sequence of SEQ ID NO: 16; and e) a second AAV ITR sequence comprising the nucleic acid sequence of SEQ ID NO: 13.

30. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 14;

c) a transgene nucleic acid molecule, wherein the transgene nucleic acid molecule comprises a nucleic acid sequence encoding for a GAT1 polypeptide, wherein the GAT1 polypeptide comprises the amino acid sequence of SEQ ID NO: 1;

d) a polyA sequence comprising the nucleic acid sequence of SEQ ID NO: 16; and e) a second AAV ITR sequence comprising the nucleic acid sequence of SEQ ID NO: 13.

31. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 15;

c) a transgene nucleic acid molecule, wherein the transgene nucleic acid molecule comprises a nucleic acid sequence encoding for a GAT1 polypeptide, wherein the GAT1 polypeptide comprises the amino acid sequence of SEQ ID NO: 1;

d) a polyA sequence comprising the nucleic acid sequence of SEQ ID NO: 16; and e) a second AAV ITR sequence comprising the nucleic acid sequence of SEQ ID NO: 13.

32. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 14;

c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence put forth in any one of SEQ ID NOs: 3-10;

d) a polyA sequence comprising the nucleic acid sequence of SEQ ID NO: 16; and e) a second AAV ITR sequence comprising the nucleic acid sequence of SEQ ID NO: 13.

33. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 15;

c) a transgene nucleic acid molecule e, wherein the transgene nucleic acid molecule comprises a nucleic acid sequence encoding for a GAT1 polypeptide, wherein the nucleic acid sequence encoding for a GAT1 polypeptide comprises the nucleic acid sequence put forth in any one of SEQ ID NOs: 3-10;

d) a polyA sequence comprising the nucleic acid sequence of SEQ ID NO: 16; and e) a second AAV ITR sequence comprising the nucleic acid sequence of SEQ ID NO: 13.

34. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 14;

c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence of SEQ ID NO: 3;

d) a polyA sequence comprising the nucleic acid sequence of SEQ ID NO: 16; and e) a second AAV ITR sequence comprising the nucleic acid sequence of SEQ ID NO: 13.

35. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 15;

c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence of SEQ ID NO: 3;

d) a polyA sequence comprising the nucleic acid sequence of SEQ ID NO: 16; and e) a second AAV ITR sequence comprising the nucleic acid sequence of SEQ ID NO: 13.

36. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 14;

c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence of SEQ ID NO: 5;

d) a polyA sequence comprising the nucleic acid sequence of SEQ ID NO: 16; and e) a second AAV ITR sequence comprising the nucleic acid sequence of SEQ ID NO: 13.

37. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 15;

c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence of SEQ ID NO: 5;

d) a polyA sequence comprising the nucleic acid sequence of SEQ ID NO: 16; and e) a second AAV ITR sequence comprising the nucleic acid sequence of SEQ ID NO: 13.

38. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 14;

c) a transgene nucleic acid molecule, wherein the transgene sequence comprises a nucleic acid nucleic acid molecule encoding for a GAT1 polypeptide, wherein the nucleic acid sequence encoding for a GAT1 polypeptide comprises the nucleic acid sequence of SEQ ID NO: 6;

d) a polyA sequence comprising the nucleic acid sequence of SEQ ID NO: 16; and e) a second AAV ITR sequence comprising the nucleic acid sequence of SEQ ID NO: 13.

39. An rAAV vector of any one of the preceding embodiments, comprising, in the 5' to 3' direction a) a first AAV ITR sequence comprising the nucleic acid sequence of SEQ ID NO: 12;

b) a promoter sequence comprising the nucleic acid sequence of SEQ ID NO: 15;

c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence of SEQ ID NO: 6;

d) a polyA sequence comprising the nucleic acid sequence of SEQ ID NO: 16; and e) a second AAV ITR sequence comprising the nucleic acid sequence of SEQ ID NO: 13.

40. An rAAV vector of any one of the preceding embodiments, wherein the rAAV vector comprises the nucleic acid sequence of SEQ ID NO: 20.

41. An rAAV vector of any one of the preceding embodiments, wherein the rAAV vector comprises the nucleic acid sequence of SEQ ID NO: 22.

42. An rAAV viral vector comprising:

a) an rAAV vector of any one of the preceding embodiments; and b) an AAV capsid protein.

43. The rAAV viral vector of embodiment 44, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

44. The rAAV viral vector of embodiment 43, wherein the AAV capsid protein is an AAV1 capsid protein.

45. The rAAV viral vector of embodiment 43, wherein the AAV capsid protein is an AAV2 capsid protein.

46. The rAAV viral vector of embodiment 43, wherein the AAV capsid protein is an AAV3 capsid protein.

47. The rAAV viral vector of embodiment 43, wherein the AAV capsid protein is an AAV4 capsid protein.

48. The rAAV viral vector of embodiment 43, wherein the AAV capsid protein is an AAV5 capsid protein.

49. The rAAV viral vector of embodiment 43, wherein the AAV capsid protein is an AAV6 capsid protein.

50. The rAAV viral vector of embodiment 43, wherein the AAV capsid protein is an AAV7 capsid protein.

51. The rAAV viral vector of embodiment 43, wherein the AAV capsid protein is an AAV8 capsid protein.

52. The rAAV viral vector of embodiment 43, wherein the AAV capsid protein is an AAV9 capsid protein.

53. The rAAV viral vector of embodiment 43, wherein the AAV capsid protein is an AAV10 capsid protein.

54. The rAAV viral vector of embodiment 43, wherein the AAV capsid protein is an AAV11 capsid protein.

55. The rAAV viral vector of embodiment 43, wherein the AAV capsid protein is an AAV12 capsid protein.

56. The rAAV viral vector of embodiment 43, wherein the AAV capsid protein is an AAV13 capsid protein.

57. The rAAV viral vector of embodiment 43, wherein the AAV capsid protein is an AAVPHP.B capsid protein.

58. The rAAV viral vector of embodiment 43, wherein the AAV capsid protein is an AAVrh74 capsid protein.

59. The rAAV viral vector of embodiment 43, wherein the AAV capsid protein is an AAVrh.10 capsid protein.

Compositions and Pharmaceutical Compositions

The present disclosure provides compositions comprising any of the isolated polynucleotides, rAAV vectors, and/or rAAV viral vectors described herein. In some aspects, the compositions can be pharmaceutical compositions. Accordingly, the present disclosure provides pharmaceutical compositions comprising any of the isolated polynucleotides, rAAV vectors, and/or rAAV viral vectors described herein.

The pharmaceutical composition, as described herein, may be formulated by any methods known or developed in the art of pharmacology, which include but are not limited to contacting the active ingredients (e.g., viral particles or recombinant vectors) with an excipient and/or additive and/or other accessory ingredient, dividing or packaging the product to a dose unit. The viral particles of this disclosure may be formulated with desirable features, e.g., increased stability, increased cell transfection, sustained or delayed release, biodistributions or tropisms, modulated or enhanced translation of encoded protein in vivo, and the release profile of encoded protein in vivo.

As such, the pharmaceutical composition may further comprise saline, lipidoids, liposomes, lipid nanoparticles, polymers, lipoplexes, core-shell nanoparticles, peptides, proteins, cells transfected with viral vectors (e.g., for transplantation into a subject), nanoparticle mimics or combinations thereof. In some aspects, the pharmaceutical composition is formulated as a nanoparticle. In some aspects, the nanoparticle is a self-assembled nucleic acid nanoparticle.

A pharmaceutical composition in accordance with the present disclosure may be prepared, packaged, and/or sold in bulk, as a single unit dose, and/or as a plurality of single unit doses. The amount of the active ingredient is generally equal to the dosage of the active ingredient which would be administered to a subject and/or a convenient fraction of such a dosage such as, for example, one-half or one-third of such a dosage. The formulations of the invention can include one or more excipients and/or additives, each in an amount that together increases the stability of the viral vector, increases cell transfection or transduction by the viral vector, increases the expression of viral vector encoded protein, and/or alters the release profile of viral vector encoded proteins. In some aspects, the pharmaceutical composition comprises an excipient and/or additive. Non limiting examples of excipients and/or additives include solvents, dispersion media, diluents, or other liquid vehicles, dispersion or suspension aids, surface active agents, isotonic agents, thickening or emulsifying agents, preservatives, or combination thereof.

In some aspects, the pharmaceutical composition comprises a cryoprotectant. The term "cryoprotectant" refers to an agent capable of reducing or eliminating damage to a substance during freezing. Non-limiting examples of cryoprotectants include sucrose, trehalose, lactose, glycerol, dextrose, raffinose and/or mannitol.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

In some aspects, a pharmaceutical composition of the present disclosure can comprise phosphate-buffered saline, D-sorbitol, sodium chloride, pluronic F-68 or any combination thereof.

In some aspects, a pharmaceutical composition can comprise sodium chloride, wherein the sodium chloride is present at a concentration of about 100 mM to about 500 mM, or about 200 mM to about 400 mM, or about 300 mM to about 400 mM. In some aspects, the sodium chloride can be present at a concentration of about 350 mM.

In some aspects, a pharmaceutical composition can comprise D-sorbitol, wherein the D-sorbitol is present at a concentration of about 1% to about 10%, or about 2.5% to about 7.5%. In some aspects, the D-sorbitol can be present at a concentration of about 5%.

In some aspects, a pharmaceutical composition can comprise pluronic F-68, wherein the pluronic F-68 is present at a concentration of about 0.00001% to about 0.01%, or about 0.0005% to about 0.005%. In some aspects, the pluronic F-68 can be present at a concentration of about 0.001%.

Thus, the present disclosure provides a pharmaceutical composition comprising an rAAV vector and/or rAAV viral vector of the present disclosure in a phosphate-buffered saline solution, wherein the pharmaceutical composition further comprises sodium chloride at a concentration of 350 mM, D-sorbitol at a concentration of 5% and pluronic F-68 at a concentration of 0.001%.

Thus, the present disclosure provides a pharmaceutical composition comprising an rAAV vector and/or rAAV viral vector of the present disclosure, wherein the pharmaceutical composition further comprises sodium chloride at a concentration of 350 mM, D-sorbitol at a concentration of 5% and pluronic F-68 at a concentration of 0.001%.

Thus, the present disclosure provides a pharmaceutical composition comprising an rAAV vector and/or rAAV viral vector of the present disclosure in a phosphate-buffered saline solution, wherein the pharmaceutical composition further comprises sodium chloride at a concentration of 350 mM, D-sorbitol at a concentration of 5%.

Thus, the present disclosure provides a pharmaceutical composition comprising an rAAV vector and/or rAAV viral vector of the present disclosure, wherein the pharmaceutical composition further comprises sodium chloride at a concentration of 350 mM, D-sorbitol at a concentration of 5%.

Methods of Using the Compositions of the Disclosure

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. Preferably, the subject is human. The terms "subject" and "patient" are used interchangeably herein.

This disclosure provides methods of preventing or treating a disorder, comprising, consisting essentially of, or consisting of administering to a subject a therapeutically effective amount of any one of the rAAV vectors, rAAV viral vectors, compositions and/or pharmaceutical compositions disclosed herein.

In some aspects, the disease can be a genetic disorder involving an SLC6A1 gene. As would be appreciated by the skilled artisan, such genetic disorders can cause one or more neurological symptoms in a subject, including, but not limited to, seizures, epilepsy, intellectual disability, schizophrenia, autism spectrum disorder (ASD), movement disorders, ataxia, tremors, behavior disorders, aggression, and/or hyperactivity, In some aspects, the epilepsy can be epilepsy with myoclonic-atonic seizures, genetic generalized epilepsy, non-acquired focal epilepsy, or any other epilepsy known in the art.

In some aspects, the seizures can be atypical absence seizures, atonic seizures, myoclonic seizures, or any other type of seizure known in the art.

In some aspects, a genetic disorder involving SLC6A1 can be SLC6A1 haploinsufficiency. As would be appreciated by the skilled artisan, SLC6A1 haploinsufficiency is also referred to as SLC6A1 epileptic encephalopathy, SLC6A1 loss of function, and GAT1 deficiency.

In some aspects, a genetic disorder involving SLC6A1 can be Doose syndrome.

In some aspects, a disease can be a disease that is characterized by the loss-of-function of at least one copy of the SLC6A1 gene in the genome of a subject. In some aspects, a disease can be a disease that is characterized by a decrease in function of at least one copy of the SLC6A1 gene in the genome of a subject. In some aspects, a disease can be a disease that is characterized by at least one mutation in at least one mutation in at least one copy of the SLC6A1 gene in the genome of the subject.

A mutation in a SLC6A1 gene can be any type of mutation that is known in the art. Non-limiting examples of mutations include somatic mutations, single nucleotide variants (SNVs), nonsense mutations, insertions, deletions, duplications, frameshift mutations, repeat expansions, short insertions and deletions (INDELs), long INDELs, alternative splicing, the products of alternative splicing, altered initiation of translation, the products of altered initiation of translation, proteomic cleavage, the products of proteomic cleavage.

In some aspects, a disease can be a disease that is characterized by a decrease in expression of the SLC6A1 gene in a subject as compared to a control subject that does not have the disease. In some aspects, the decrease in expression can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the amount of GAT1 in a subject as compared to a control subject that does not have the disease. In some aspects, the decrease in the amount of GAT1 can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the activity of GAT1 in a subject as compared to a control subject that does not have the disease. In some aspects, the decrease in the activity of GAT1 can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in reuptake of the GABA neurotransmitter from the synaptic cleft as compared to a control subject that does not have the disease. In some aspects, the decrease in reuptake can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

A subject to be treated using the methods, compositions, pharmaceutical compositions, rAAV vectors or rAAV viral vectors of the present disclosure can have any of the diseases and/or symptoms described herein.

In some aspects, a subject can be less than 0.5 years of age, or less than 1 year of age, or less than 1.5 years of age, or less than 2 years of age, or at less than 2.5 years of age, or less than 3 years of age, or less than 3.5 years of age, or less than 3.5 years of age, or less than 4 years of age, or less than 4.5 years of age, or less than 5 years of age, or less than 5.5 years of age, or less than 6 years of age, or less than 6.5 years of age, or less than 7 years of age, or less than 7.5 years of age, or less than 8 years of age, or less than 8.5 years of age, or less than 9 years of age, or less than 9.5 years of age, or less than 10 years of age. In some aspects the subject can be less than 11 years of age, less than 12 years of age, less than 13 years of age, less than 14 years of age, less than 15 years of age, less than 20 years of age, less than 30 years of age, less than 40 years of age, less than 50 years of age, less than 60 years of age, less than 70 years of age, less than 80 years of age, less than 90 years of age, less than 100 years of age, less than 110 years of age, or less than 120 years of age. In some aspects, a subject can be less than 0.5 years of age. In some aspects, a subject can be less than 4 years of age. In some aspects, a subject can be less than 10 years of age.

The methods of treatment and prevention disclosed herein may be combined with appropriate diagnostic techniques to identify and select patients for the therapy or prevention.

The disclosure provides methods of increasing the level of a protein in a host cell, comprising contacting the host cell with any one of the rAAV viral vectors disclosed herein, wherein the rAAV viral vectors comprises any one of the rAAV vectors disclosed herein, comprising a transgene nucleic acid molecule encoding the protein. In some aspects, the protein is a therapeutic protein. In some aspects, the host cell is in vitro, in vivo, or ex vivo. In some aspects, the host cell is derived from a subject. In some aspects, the subject suffers from a disorder, which results in a reduced level and/or functionality of the protein, as compared to the level and/or functionality of the protein in a normal subject.

In some aspects, the level of the protein is increased to level of about $1\times10^{-7}$ ng, about $3\times10^{-7}$ ng, about $5\times10^{-7}$ ng, about $7\times10^{-7}$ ng, about $9\times10^{-7}$ ng, about $1\times10^{-6}$ ng, about $2\times10^{-7}$ ng, about $3\times10^{-7}$ ng, about $4\times10^{-7}$ ng, about $6\times10^{-7}$ ng, about $7\times10^{-6}$ ng, about $8\times10^{-7}$ ng, about $9\times10^{-7}$ ng, about $10\times10^{-7}$ ng, about $12\times10^{-7}$ ng, about $14\times10^{-7}$ ng, about $16\times10^{-7}$ ng, about $18\times10^{-6}$ ng, about $20\times10^{-6}$ ng, about $25\times10^{-6}$ ng, about $30\times10^{-6}$ ng, about $35\times10^{-6}$ ng, about $40\times10^{-6}$ ng, about $45\times10^{-6}$ ng, about $50\times10^{-6}$ ng, about $55\times10^{-6}$ ng, about $60\times10^{-6}$ ng, about $65\times10^{-6}$ ng, about $70\times10^{-6}$ ng, about $75\times10^{-6}$ ng, about $80\times10^{-6}$ ng, about $85\times10^{-6}$ ng, about $90\times10^{-6}$ ng, about $95\times10^{-6}$ ng, about $10\times10^{-5}$ ng, about $20\times10^{-5}$ ng, about $30\times10^{-5}$ ng, about $40\times10^{-5}$ ng, about $50\times10^{-5}$ ng, about $60\times10^{-5}$ ng, about $70\times10^{-5}$ ng, about $80\times10^{-5}$ ng, or about $90\times10^{-5}$ ng in the host cell.

The disclosure provides methods of introducing a gene of interest to a cell in a subject comprising contacting the cell with an effective amount of any one of the rAAV viral vectors disclosed herein, wherein the rAAV viral vectors contain any one of the rAAV vectors disclosed herein, comprising the gene of interest.

In some aspects of the methods of the present disclosure, a subject can also be administered a prophylactic immunosuppressant treatment regimen in addition to being administered an rAAV vector or rAAV viral vector of the present disclosure. In some aspects, an immunosuppressant treatment regimen can comprise administering at least one immunosuppressive therapeutic. Non limiting examples of immunosuppressive therapeutics include, but are not limited to, Sirolimus (rapamycin), acetaminophen, diphenhydramine, IV methylprednisolone, prednisone, or any combination thereof. An immunosuppressive therapeutic can be administered prior to the day of administration of the rAAV vector and/or rAAV viral vector, on the same day as the administration of the rAAV vector and/or rAAV viral vector, or any day following the administration of the rAAV vector and/or rAAV viral vector.

A "subject" of diagnosis or treatment is a cell or an animal such as a mammal, or a human. A subject is not limited to a specific species and includes non-human animals subject to diagnosis or treatment and those subject to infections or animal models, including, without limitation, simian, murine, rat, canine, or leporid species, as well as other livestock, sport animals, or pets. In some aspects, the subject is a human.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein the term "effective amount" intends to mean a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of gene therapy, the effective amount can be the amount sufficient to result in regaining part or full function of a gene that is deficient in a subject. In some aspects, the effective amount of an rAAV viral vector is the amount sufficient to result in expression of a gene in a subject such that GAT1 is produced. In some aspects, the effective amount is the amount required to increase galactose metabolism in a subject in need thereof. The skilled artisan will be able to determine appropriate amounts depending on these and other factors.

In some aspects, the effective amount will depend on the size and nature of the application in question. It will also depend on the nature and sensitivity of the target subject and the methods in use. The skilled artisan will be able to determine the effective amount based on these and other considerations. The effective amount may comprise, consist essentially of, or consist of one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and other animals, treating veterinarian.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as $10^9$ vector genomes to as much as $10^{17}$ vector genomes per administration.

In some aspects of the methods described herein, the number of viral particles (e.g., rAAV viral vectors) administered to the subject ranges from about $10^9$ to about $10^{17}$. In some aspects, about $10^{10}$ to about $10^{12}$, about $10^{11}$ to about $10^{13}$, about $10^{11}$ to about $10^{12}$, about $10^{11}$ to about $10^{14}$, about $10^{12}$ to about $10^{16}$, about $10^{13}$ to about $10^{16}$, about $10^{14}$ to about $10^{15}$, about $5\times10^{11}$ to about $5\times10^{12}$, or about $10^{12}$ to about $10^{13}$ viral particles are administered to the subject.

In some aspects of the methods described herein, the number of viral particles (e.g., rAAV viral vectors) administered to the subject is at least about $10^{10}$, or at least about $10^{11}$, or at least about $10^{12}$, or at least about $10^{13}$, or at least about $10^{14}$, or at least about $10^{15}$, or at least about $10^{16}$, or at least about $10^{17}$ viral particles.

In some aspects of the methods described herein, the number of viral particles (e.g., rAAV viral vectors) administered to the subject can depend on the age of the subject. In non-limiting examples, a subject that is 7 years of age or older can be administered about $10\times10^{14}$ viral particles, a subject that is about 4 years of age to about 7 years of age can be administered about $10\times10^{14}$ viral particles, a subject that is about 3 years of age to about 4 years of age can be administered about $9\times10^{14}$ viral particles, a subject that is about 2 years of age to about 3 years of age can be about $8.2\times10^{14}$ viral particles, a subject that is about 1 year of age to about 2 years of age can be administered about $7.3\times10^{14}$ viral particles, a subject that is about 0.5 years of age to about 1 year of age can be administered about $4\times10^{14}$ viral particles, or a subject that is less than 0.5 years of age can be administered $3\times10^{14}$ viral particles.

In some aspects, the amounts of viral particles in a composition, pharmaceutical composition, or the amount of viral particles administered to a patient can calculated based on the percentage of viral particles that are predicted to contain viral genomes.

In some aspects, rAAV viral vectors of the present disclosure can be introduced to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally; such introduction may also be intra-arterial, intracardiac, subventricular, epidural, intracerebral, intracerebroventricular, sub-retinal, intravitreal, intraarticular, intraperitoneal, intrauterine, intranerve or any combination thereof. In some aspects, the viral particles are delivered to a desired target tissue, e.g., to the lung, eye, or CNS, as non-limiting examples. In some aspects, delivery of viral particles is systemic. The intracisternal route of administration involves administration of a drug directly into the cerebrospinal fluid of the brain ventricles. It could be performed by direct injection into the cisterna magna or via a permanently positioned tube. In some aspects, the rAAV viral vectors of the present disclosure are administered intrathecally.

In some aspects, the rAAV viral vectors of the present disclosure repair a gene deficiency in a subject. In some aspects, the ratio of repaired target polynucleotide or polypeptide to unrepaired target polynucleotide or polypeptide in a successfully treated cell, tissue, organ or subject is at least about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to western blot, northern blot, Southern blot, PCR, sequencing, mass spectrometry, flow cytometry, immunohistochemistry, immunofluorescence, fluorescence in situ hybridization, next generation sequencing, immunoblot, and ELISA.

Administration of the rAAV vectors, rAAV viral vectors, compositions or pharmaceutical compositions of this disclosure can be effected in one dose, continuously or intermittently throughout the course of treatment. In some aspects, the rAAV vectors, rAAV viral vectors, compositions, or pharmaceutical compositions of this disclosure are parenterally administered by injection, infusion, or implantation.

In some aspects, the rAAV viral vectors of this disclosure show enhanced tropism for brain and cervical spine. In some aspects, the rAAV viral vectors of the disclosure can cross the blood-brain-barrier (BBB).

Methods of Manufacture

A variety of approaches may be used to produce rAAV viral vectors of the present disclosure. In some aspects, packaging is achieved by using a helper virus or helper plasmid and a cell line. The helper virus or helper plasmid contains elements and sequences that facilitate viral vector production. In another aspect, the helper plasmid is stably incorporated into the genome of a packaging cell line, such that the packaging cell line does not require additional transfection with a helper plasmid.

In some aspects, the cell is a packaging or helper cell line. In some aspects, the helper cell line is eukaryotic cell; for example, an HEK 293 cell or 293T cell. In some aspects, the helper cell is a yeast cell or an insect cell.

In some aspects, the cell comprises a nucleic acid encoding a tetracycline activator protein; and a promoter that regulates expression of the tetracycline activator protein. In some aspects, the promoter that regulates expression of the tetracycline activator protein is a constitutive promoter. In some aspects, the promoter is a phosphoglycerate kinase promoter (PGK) or a CMV promoter.

A helper plasmid may comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication-competent AAV.

Helper plasmids for packaging AAV are known in the art, see, e.g., U.S. Patent Pub. No. 2004/0235174 A1, incorporated herein by reference. As stated therein, an AAV helper plasmid may contain as helper virus DNA sequences, by way of non-limiting example, the Ad5 genes E2A, E4 and VA, controlled by their respective original promoters or by heterologous promoters. AAV helper plasmids may additionally contain an expression cassette for the expression of a marker protein such as a fluorescent protein to permit the simple detection of transfection of a desired target cell.

The disclosure provides methods of producing rAAV viral vectors comprising transfecting a packaging cell line with any one of the AAV helper plasmids disclosed herein; and any one of the rAAV vectors disclosed herein. In some aspects, the AAV helper plasmid and rAAV vector are co-transfected into the packaging cell line. In some aspects, the cell line is a mammalian cell line, for example, human embryonic kidney (HEK) 293 cell line. The disclosure provides cells comprising any one of the rAAV vectors and/or rAAV viral vectors disclosed herein.

As used herein, the term "helper" in reference to a virus or plasmid refers to a virus or plasmid used to provide the additional components necessary for replication and packaging of any one of the rAAV vectors disclosed herein. The components encoded by a helper virus may include any genes required for virion assembly, encapsidation, genome replication, and/or packaging. For example, the helper virus or plasmid may encode necessary enzymes for the replication of the viral genome. Non-limiting examples of helper viruses and plasmids suitable for use with AAV constructs include pHELP (plasmid), adenovirus (virus), or herpesvirus (virus). In some aspects, the pHELP plasmid may be the pHELPK plasmid, wherein the ampicillin expression cassette is exchanged with a kanamycin expression cassette.

As used herein, a packaging cell (or a helper cell) is a cell used to produce viral vectors. Producing recombinant AAV viral vectors requires Rep and Cap proteins provided in trans as well as gene sequences from Adenovirus that help AAV replicate. In some aspects, Packaging/helper cells contain a plasmid is stably incorporated into the genome of the cell. In other aspects, the packaging cell may be transiently transfected. Typically, a packaging cell is a eukaryotic cell, such as a mammalian cell or an insect cell.

Kits

The isolated polynucleotides, rAAV vectors, rAAV viral vectors, compositions, and/or pharmaceutical compositions described herein may be assembled into pharmaceutical or diagnostic or research kits to facilitate their use in therapeutic, diagnostic, or research applications. In some aspects, the kits of the present disclosure include any one of the isolated polynucleotides, rAAV vectors, rAAV viral vectors, compositions, pharmaceutical compositions, host cells, isolated tissues, as described herein.

In some aspects, a kit further comprises instructions for use. Specifically, such kits may include one or more agents described herein, along with instructions describing the intended application and the proper use of these agents. In some aspects, the kit may include instructions for mixing one or more components of the kit and/or isolating and mixing a sample and applying to a subject. In some aspects, agents in a kit are in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. In some aspects, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In some aspects, the preservation solution contains an amount of metalloprotease inhibitors.

In some aspects, the kit contains any one or more of the components described herein in one or more containers. Thus, in some aspects, the kit may include a container housing agents described herein. The agents may be in the form of a liquid, gel or solid (powder). The agents may be prepared sterilely, packaged in a syringe and shipped refrigerated. Alternatively, they may be housed in a vial or other container for storage. A second container may have other agents prepared sterilely. Alternatively, the kit may include the active agents premixed and shipped in a syringe, vial, tube, or other container. The kit may have one or more or all of the components required to administer the agents to a subject, such as a syringe, topical application devices, or IV needle tubing and bag.

Further Definitions

Unless the context indicates otherwise, it is specifically intended that the various features of the invention described herein can be used in any combination. Moreover, the disclosure also contemplates that, in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified aspects, embodiments, features, and terms intend to include both the recited aspect, embodiment, feature, or term and biological equivalents thereof.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (RI. Freshney, ed. (1987)).

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure. In each instance herein any of the terms "comprising," "consisting essentially of," and "consisting of" can be replaced with either of the other two terms, while retaining their ordinary meanings.

All numerical designations, e.g., pH, temperature, time, concentration, and molecular weight, including ranges, are approximations which are varied (+) or (−) by increments of 1.0 or 0.1, as appropriate, or, alternatively, by a variation of +/−15%, 10%, 5%, 2%. It is to be understood, although not always explicitly stated, that all numerical designations are preceded by the term "about". It also is to be understood, although not always explicitly stated, that the reagents described herein are merely exemplary and that equivalents of such are known in the art. The term "about," as used herein when referring to a measurable value such as an amount or concentration and the like, is meant to encompass variations of 20%, 10%, 5%, 1%, 0.5%, or even 0.1% of the specified amount.

The terms "acceptable," "effective," or "sufficient" when used to describe the selection of any components, ranges, dose forms, etc. disclosed herein intend that said component, range, dose form, etc. is suitable for the disclosed purpose.

Also, as used herein, "and/or" refers to and encompasses any and all possible combinations of one or more of the associated listed items, as well as the lack of combinations when interpreted in the alternative ("or").

Unless specifically recited, the term "host cell" includes a eukaryotic host cell, including, for example, fungal cells, yeast cells, higher plant cells, insect cells and mammalian cells. Non-limiting examples of eukaryotic host cells include simian, bovine, porcine, murine, rat, avian, reptilian and human, e.g., HEK293 cells and 293T cells.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising, consisting essentially of, or consisting of purine and pyrimidine bases or other natural, chemically or biochemically modified, non-natural, or derivatized nucleotide bases.

A "gene" refers to a polynucleotide containing at least one open reading frame (ORF) that is capable of encoding a particular polypeptide or protein. A "gene product" or, alternatively, a "gene expression product" refers to the amino acid sequence (e.g., peptide or polypeptide) generated when a gene is transcribed and translated.

As used herein, "expression" refers to the two-step process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell.

"Under transcriptional control" is a term well understood in the art and indicates that transcription of a polynucleotide sequence, usually a DNA sequence, depends on its being operatively linked to an element that contributes to the initiation of, or promotes, transcription. "Operatively linked" intends that the polynucleotides are arranged in a manner that allows them to function in a cell. In one aspect, promoters can be operatively linked to the downstream sequences.

The term "encode" as it is applied to polynucleotides and/or nucleic acid sequences refers to a polynucleotide and/or nucleic acid sequence which is said to "encode" a polypeptide if, in its native state or when manipulated by methods well known to those skilled in the art, it can be transcribed to produce the mRNA for the polypeptide and/or a fragment thereof. The antisense strand is the complement of such a nucleic acid, and the encoding sequence can be deduced therefrom.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise, consist essentially of, or consist of a protein's or peptide's sequence. As used herein the term "amino acid" refers to either natural and/or unnatural or synthetic amino acids, including glycine and both the D and L optical isomers, amino acid analogs and peptidomimetics.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some aspects, the signal peptide is removed following localization. Examples of signal peptides are well known in the art. Non-limiting examples are those described in U.S. Pat. Nos. 8,853,381, 5,958,736, and 8,795,965. In some aspects, the signal peptide can be an IDUA signal peptide.

The terms "equivalent" or "biological equivalent" are used interchangeably when referring to a particular molecule, biological material, or cellular material and intend those having minimal homology while still maintaining desired structure or functionality. Non-limiting examples of equivalent polypeptides include a polypeptide having at least about 60%, at least about 65%, at least about 70%, at least about 75%, at least about 80%, at least about 85%, at least about 90%, at least about 95% identity or at least about 99% identity to a reference polypeptide (for instance, a wild-type polypeptide); or a polypeptide which is encoded by a polynucleotide having at least about 70%, at least about 75%, at least about 80%, at least about 85%, at least about 90%, at least about 95% identity, at least about 97% sequence identity or at least about 99% sequence identity to the reference polynucleotide (for instance, a wild-type polynucleotide).

"Homology" or "identity" or "similarity" refers to sequence similarity between two peptides or between two nucleic acid molecules. Percent identity can be determined by comparing a position in each sequence that may be aligned for purposes of comparison. When a position in the compared sequence is occupied by the same base or amino acid, then the molecules are identical at that position. A degree of identity between sequences is a function of the number of matching positions shared by the sequences. "Unrelated" or "non-homologous" sequences share less than 40% identity, less than 25% identity, with one of the sequences of the present disclosure. Alignment and percent sequence identity may be determined for the nucleic acid or amino acid sequences provided herein by importing said nucleic acid or amino acid sequences into and using ClustalW (available at https://genome.jp/tools-bin/clustalw/). For example, the ClustalW parameters used for performing the protein sequence alignments found herein were generated using the Gonnet (for protein) weight matrix. In some aspects, the ClustalW parameters used for performing nucleic acid sequence alignments using the nucleic acid sequences found herein are generated using the ClustalW (for DNA) weight matrix.

As used herein, amino acid modifications may be amino acid substitutions, amino acid deletions or amino acid insertions. Amino acid substitutions may be conservative amino acid substitutions or non-conservative amino acid substitutions. A conservative replacement (also called a conservative mutation, a conservative substitution or a conservative variation) is an amino acid replacement in a protein that changes a given amino acid to a different amino acid with similar biochemical properties (e.g., charge, hydrophobicity or size). As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one charged or polar residue for another, such as the substitution of arginine for lysine, glutamic acid for aspartic acid, glutamine for asparagine, and the like. Other illustrative examples of conservative substitutions include the changes of: alanine to serine; asparagine to glutamine or histidine; aspartate to glutamate; cysteine to serine; glycine to proline; histidine to asparagine or glutamine; lysine to arginine, glutamine, or glutamate; phenylalanine to tyrosine, serine to threonine; threonine to serine; tryptophan to tyrosine; tyrosine to tryptophan or phenylalanine; and the like.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

A "plasmid" is a DNA molecule that is typically separate from and capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or, alternatively, the proteins produced may act as toxins under similar circumstances. It is known in the art that while plasmid vectors often exist as extrachromosomal circular DNA molecules, plasmid vectors may also be designed to be stably integrated into a host chromosome either randomly or in a targeted manner, and such integration may be accomplished using either a circular plasmid or a plasmid that has been linearized prior to introduction into the host cell.

"Plasmids" used in genetic engineering are called "plasmid vectors". Many plasmids are commercially available for such uses. The gene to be replicated is inserted into copies of a plasmid containing genes that make cells resistant to particular antibiotics, and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria or eukaryotic cells containing a plasmid harboring the gene of interest, which can be induced to produce large amounts of proteins from the inserted gene.

In aspects where gene transfer is mediated by a DNA viral vector, such as an adenovirus (Ad) or adeno-associated virus (AAV), a vector construct refers to the polynucleotide comprising, consisting essentially of, or consisting of the viral genome or part thereof, and a transgene.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected), or a group of tissues making up an organ or part or region of the body of an organism. The tissue may comprise, consist essentially of, or consist of a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

EXAMPLES

Example 1: Codon Optimization of a Transgene Nucleic Acid Molecule Comprising a Nucleic Acid Sequence Encoding a GAT1 Polypeptide A transgene nucleic acid molecule comprising a codon optimized nucleic acid sequence encoding a GAT1 polypeptide was designed. The codon optimized nucleic acid sequence was codon optimized to facilitate the ease of transgene detection by molecular methods and minimize rare unrelated transcripts or aberrant splicing variants. The codon optimized nucleic acid sequence was optimized to remove rare codons, cryptic splice sites, and cryptic start sites with an altered nucleic acid sequence that still encodes the fully WT polypeptide. The codon optimization also allows for easier tracking of the transgene sequence to distinguish it from the endogenous chromosomal gene sequence in vivo. Molecular methods such as polymerase chain reaction, Southern blot, Northern blot, in situ hybridization, etc. can thus be used to readily detect the distribution of the vector transgene and expressed transgene mRNA in cells, tissues, or body fluids. These changes may also increase expression and may also reduce expression of alternative proteins that could be immunogenic or otherwise detrimental compared to the natural unmodified gene sequence.

Example 2—the rAAV Viral Vectors of the Present Disclosure Increases Expression of SCL6A1 in the Brain The following is a non-limiting example that demonstrates that the compositions and methods of the present disclosure can be used to increase expression of SCL6A1 in brain tissue.

Wildtype mice were administered by intrathecal injection an rAAV viral vector, hereafter referred to as "AAV9/JeT-SLC6A1", comprising: i) an rAAV vector comprising the nucleic acid sequence set forth in SEQ ID NO: 20. Specifically, the rAAV vector comprised, in the 5' to 3' direction, a first AAV ITR (SEQ ID NO: 12), a JeT promoter sequence (SEQ ID NO: 14), a transgene nucleic acid molecule comprising a codon-optimized nucleic acid sequence that encodes for a GAT1 polypeptide (SEQ ID NO: 3), a SV40pA sequence (SEQ ID NO: 16) and a second AAV ITR (SEQ ID NO: 13).

The mice were sacrificed at 6 months post-injection to analyze the expression of the codon optimized SLC6A1 transgene mRNA by RNAscope. Five micron paraffin-embedded sagittal sections through the entire brain were labeled with an RNAscope probe that specifically hybridizes to the codon-optimized SLC6A1 transgene mRNA only. A representative image of the RNAscope analysis is shown in FIG. 1. The RNAscope data showed that the codon optimized SLC6A1 was expressed throughout the brain tissue and that this expression was persistent for at least 6 months. Thus, these results indicate that the rAAV viral vectors of present disclosure can be used to drive widespread and persistent expression of SLC6A1 in brain tissue.

Example 3—Behavioral Rescue in SLC6A1 Deficient Mice Using the Compositions and Methods of the Present Disclosure The following is a non-limiting example that demonstrates the compositions and methods of the present disclosure can be used to treat diseases and/or disorders that are characterized by the loss-of-function of at least one copy of the SLC6A1 gene in the genome of a subject.

In this example, SLC6A1 knockout (KO) mice were administered one of the following treatments via intrathecal injection at 7-10 days of age:

a) a vehicle control;
b) an rAAV viral vector, hereafter referred to as "AAV9/JeT-SLC6A1", comprising:
  i) an rAAV vector comprising the nucleic acid sequence set forth in SEQ ID NO: 20. Specifically, the rAAV vector comprised, in the 5' to 3' direction, a first AAV ITR (SEQ ID NO: 12), a JeT promoter sequence (SEQ ID NO: 14), a transgene nucleic acid molecule comprising a codon-optimized nucleic acid sequence that encodes for a GAT1 polypeptide (SEQ ID NO: 3), a SV40pA sequence (SEQ ID NO: 16) and a second AAV ITR (SEQ ID NO: 13); and
  ii) an AAV9 capsid protein; or
c) an rAAV viral vector, hereafter referred to as "AAV9/MeP-SLC6A1", comprising:
  i) an rAAV vector comprising the nucleic acid sequence set forth in SEQ ID NO: 22. Specifically, the rAAV vector comprised, in the 5' to 3' direction, a first AAV ITR (SEQ ID NO: 12), a mEP229 promoter sequence (SEQ ID NO: 15), a transgene nucleic acid molecule comprising a codon-optimized nucleic acid sequence that encodes for a GAT1 polypeptide (SEQ ID NO: 3), a SV40pA sequence (SEQ ID NO: 16) and a second AAV ITR (SEQ ID NO: 13); and ii) an AAV9 capsid protein.

Figure 2:
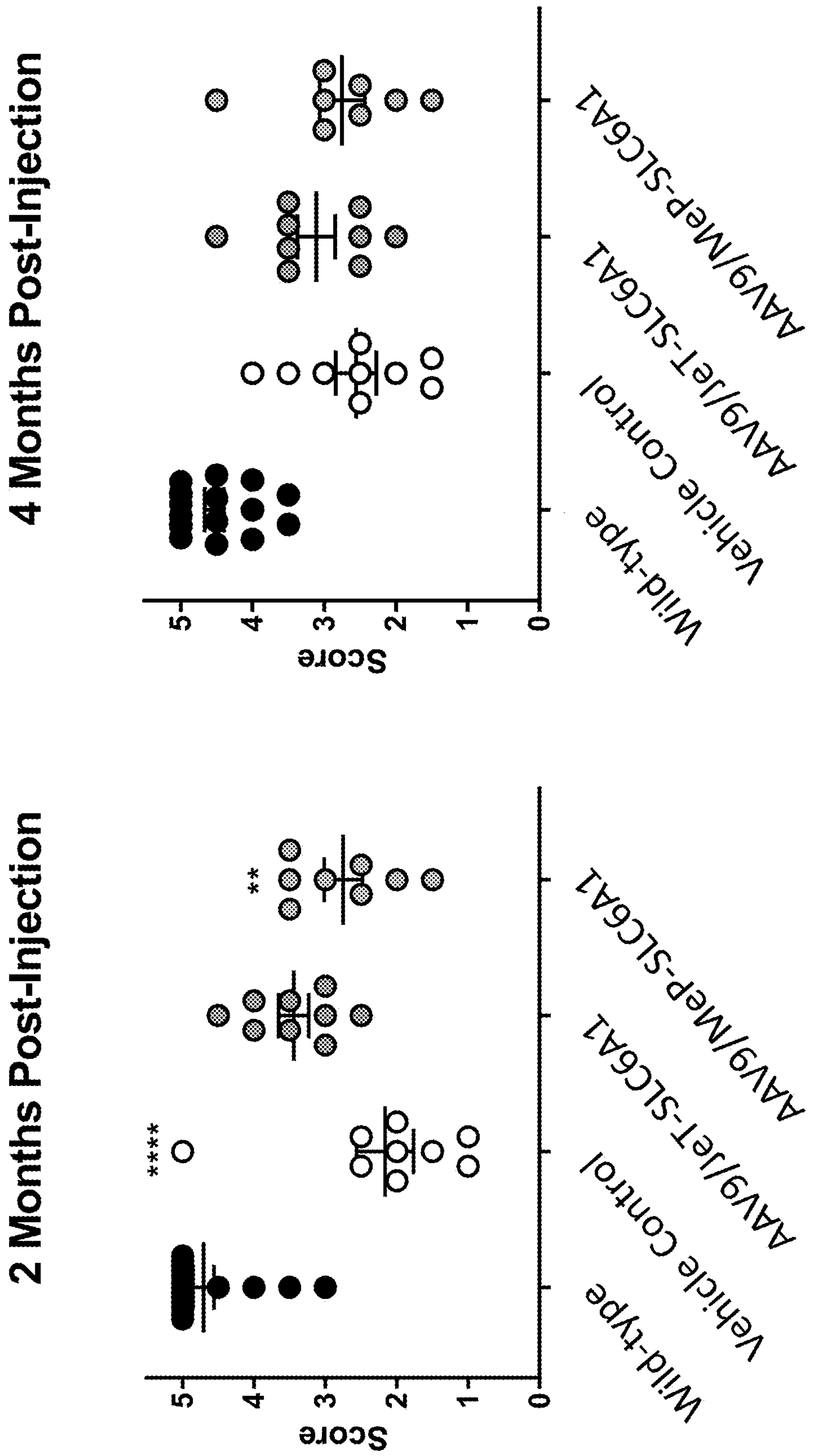
FIG. 2 is a series of graphs showing the nest-building scores of untreated wildtype mice, SLC6A1 knockout (KO) mice treated with a vehicle control, SLC6A1 KO mice treated with the AAV9/JeT-SLC6A1 viral vector (as described herein), and SLC6A1 KO mice treated with the AAV9/MeP-SLC6A1 viral vector (as described herein). The nest building scores were recorded 2 months post-injection (left graph) and 4 months post-injection (right graph). $^{}p<0.01$ compared to WT, $^{**}p<0.0001$ compared to WT control.

Nest building activity of the treated mice was analyzed at 2 months post-injection and 4 months post-injection. Nest building activity of wildtype mice was also analyzed as a control for comparison. FIG. 2 shows the nest building scores measured at 2 months post-injection and 4 months post-injection. As shown in FIG. 2, there was an improvement in the nest building scores at 2 months post-injection in mice administered AAV9/JeT-SLC6A1 and AAV9/MeP-SLC6A1. By 4-months post-injection, all SLC6A1 KO mice showed improvement in nest building scores, indicating that while SLC6A1 KO can improve with repeated testing, treated KO mice learn this behavior earlier than untreated KO mice.

Figure 3:
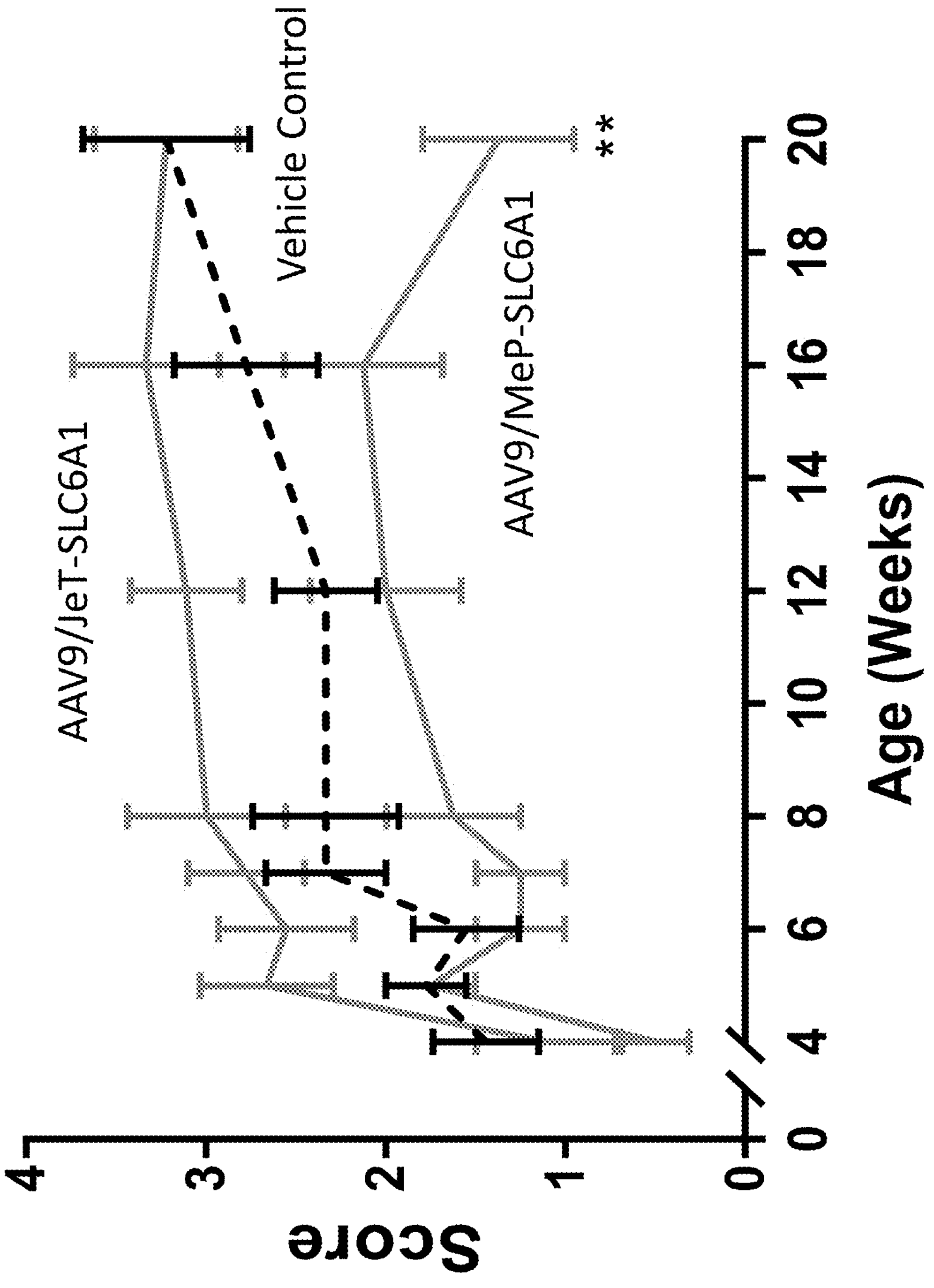
FIG. 3 is a graph showing hind limb clasping scores in SLC6A1 knockout (KO) mice treated with a vehicle control, SLC6A1 KO mice treated with the AAV9/JeT-SLC6A1 viral vector (as described herein), and SLC6A1 KO mice treated with the AAV9/MeP-SLC6A1 viral vector (as described herein) over the course of 20 weeks after viral vector injection. $^{**}p<0.01$ compared to Vehicle control.

Hind limb clasping activity was also analyzed in the treated mice over the course of 20 weeks following injection. The results of the hind limb clasping activity analysis are shown in FIG. 3. As shown in FIG. 3, improvement in hindlimb clasping was observed in mice treated with AAV9/MeP-SLC6A1 vector at 20 weeks post-injection.

Figure 4:
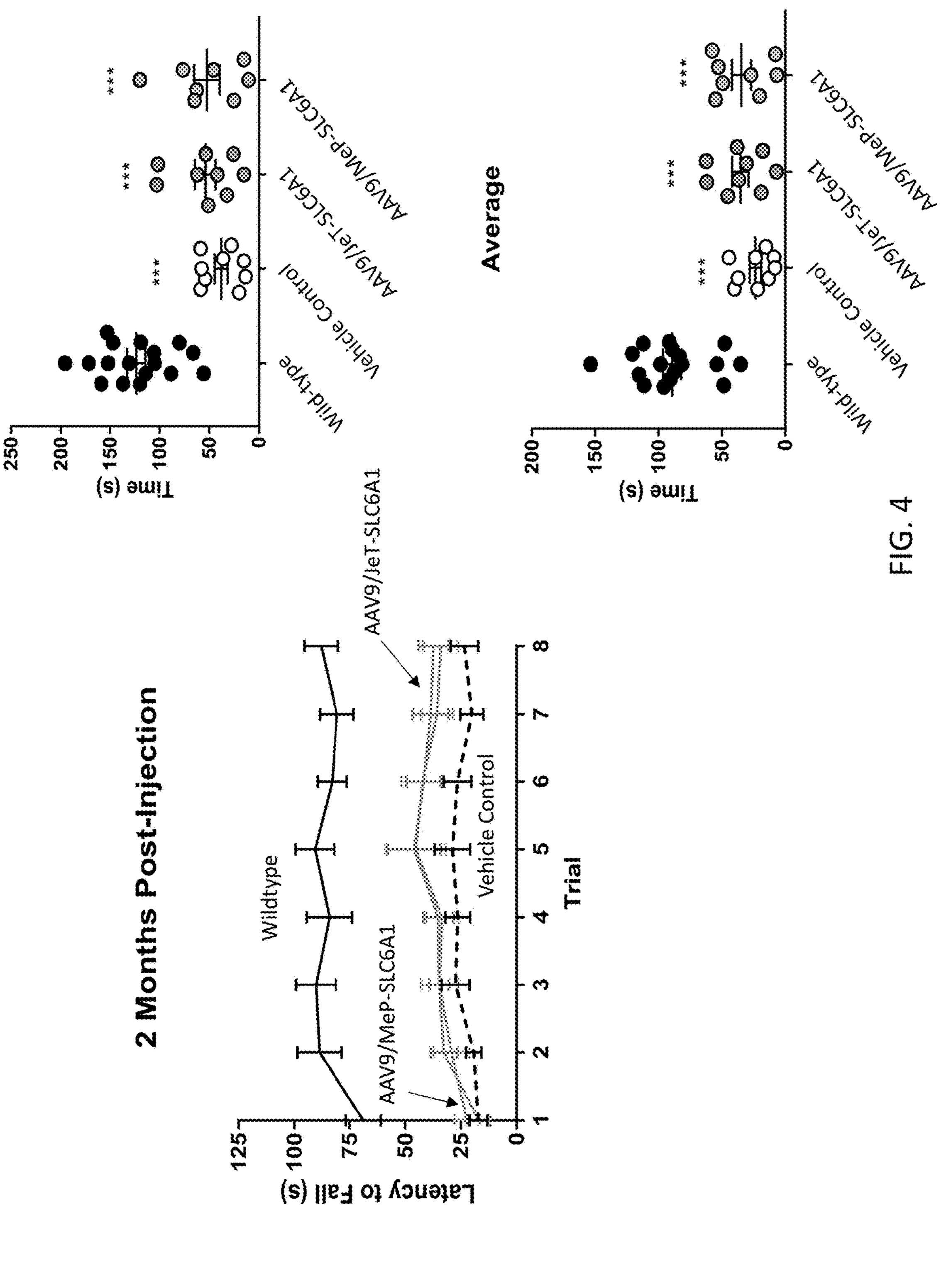
FIG. 4 is a series of graphs showing the rotarod performance of untreated wildtype mice, SLC6A1 knockout (KO) mice treated with a vehicle control, SLC6A1 KO mice treated with the AAV9/JeT-SLC6A1 viral vector (as described herein), and SLC6A1 KO mice treated with the AAV9/MeP-SLC6A1 viral vector (as described herein), 2 months after viral vector injection. $^{***}p<0.001$ compared to wildtype control.
Figure 5:
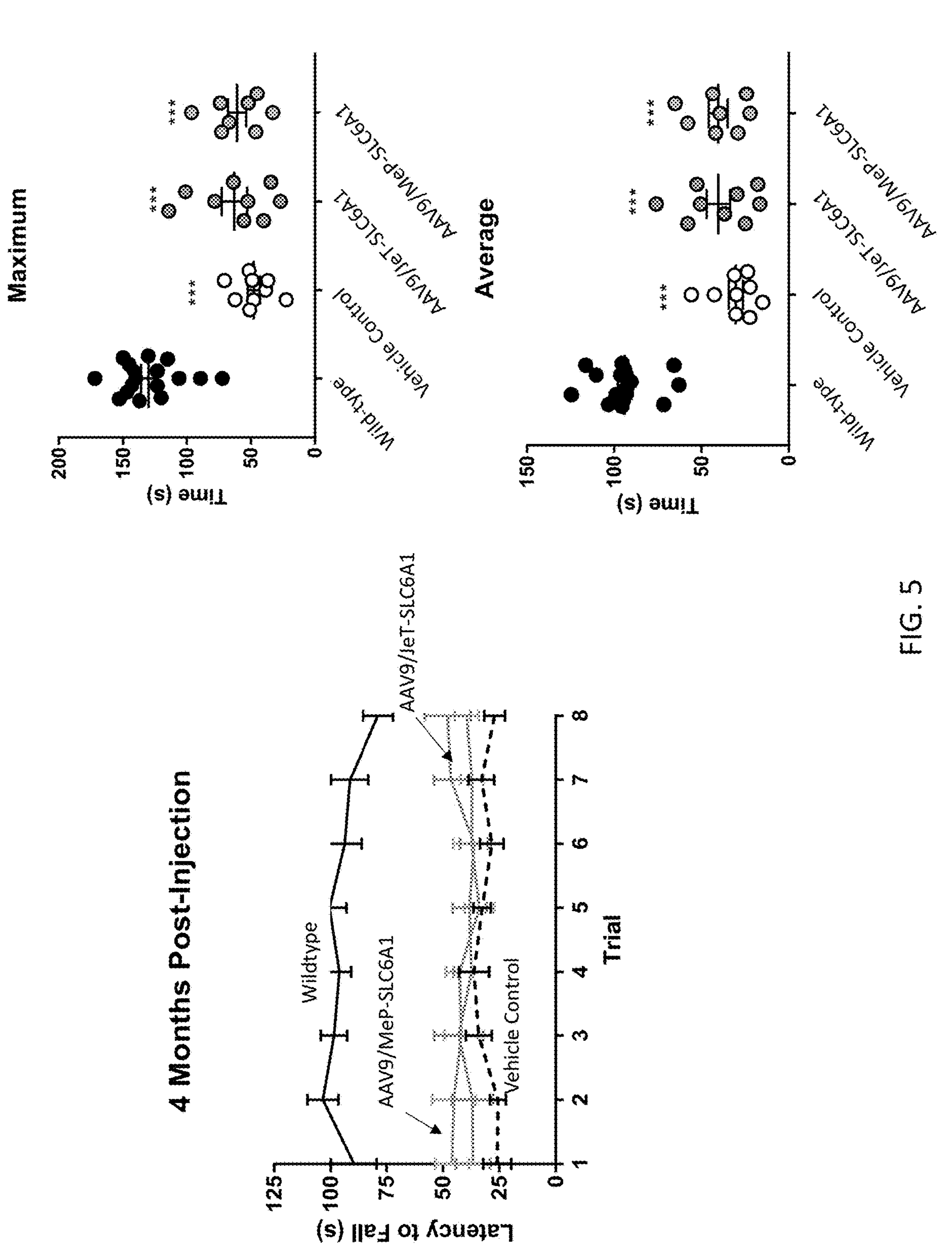
FIG. 5 is a series of graphs showing the rotarod performance of untreated wildtype mice, SLC6A1 knockout (KO) mice treated with a vehicle control, SLC6A1 KO mice treated with the AAV9/JeT-SLC6A1 viral vector (as described herein), and SLC6A1 KO mice treated with the AAV9/MeP-SLC6A1 viral vector (as described herein), 4 months after viral vector injection. $^{***}p<0.001$ compared to wildtype control.

Finally, rotarod performance of the treated mice was analyzed at 2 months post-injection and 4 months post-injection. Rotarod performance of wildtype mice was also analyzed as a control for comparison. The results of the rotarod performance analysis are shown in FIG. 4 (2 months post-injection) and FIG. 5 (4 months post-injection. As shown in FIG. 4 and FIG. 5, SLC6A1 KO mice treated with either AAV9/JeT-SLC6A1 or AAV9/MeP-SLC6A1 showed improvements in latency to fall as compared to the SLC6A1 KO mice that were treated with vehicle control.

As would be appreciated by the skilled artisan, the phenotype of SLC6A1 KO mice is significantly more severe than the phenotype of human diseases and/or disorders that are characterized by the loss-of-function of at least one copy of the SLC6A1 gene. Thus, the behavioral improvements in the SLC6A1 KO mice upon administration of either AAV9/JeT-SLC6A1 or AAV9/MeP-SLC6A1 demonstrate that rAAV viral vectors can be used to treat SLC6A1-associated diseases and disorders in a human subject.

Example 4—Toxicology Studies Using the rAAV Viral Vectors of the Present Disclosure The following is a non-limiting example of a study designed to test the toxicity of the rAAV viral vectors of the present disclosure.

Mice were treated with a vehicle control, AAV9/MeP-SLC6A1 (as described above) or AAV9/JeT-SLC6A1 (as described above) as set forth in Table 1.

TABLE 1

| Age at Treatment (Days) | Mice/Group (M/F) | Viral Vector | Dose Group | Dose/ mouse (vg × $10^{11}$) | In Life Assessment | Terminal Assessment |
|---|---|---|---|---|---|---|
| 28-35 | 12 (6/6) | AAV9/JeT-SLC6A1 | High<br>Low | 7.5<br>1.88 | Body weights, clinical signs, adverse events, mortality, serology 3 weeks post-injection | Serology, histopathology, transgene expression; 12 months post-injection |
| | | AAV9/MeP-SLC6A1 | High<br>Low | 7<br>1.75 | | |
| | | na | Vehicle | — | | |
| 7-10 | 12 (6/6) | AAV9/JeT-SLC6A1 | High<br>Low | 7.5<br>1.88 | Body weights, clinical signs, adverse events, mortality | Serology, histopathology, transgene expression; 6 months post-injection |
| | | AAV9/MeP-SLC6A1 | High<br>Low | 7<br>1.75 | | |
| | | na | Vehicle | — | | |

IT injections via lumbar puncture, a 5 μL dose in vehicle (350 mM phosphate-buffered saline, 5% sorbitol).

Body weight differences were monitored over the course of the study to assess the overall health of the mice. There were no significant differences in the body weights of the different treatment cohorts at the time of the last assessment. At 7 months post-injection, the mice did not show any outward signs of toxicity. Additionally, there were no obvious signs of morbidity in the adult wild-type mice dosed with AAV9/JeT-SLC6A1 or AAV9/MeP-SLC6A1 at either the high or low doses.

Blood was collected in the P28-35 injected mice 3 weeks post-injection and analyzed for multiple markers including aspartate aminotransferase, blood urea nitrogen, albumin, creatine kinase and total bilirubin. The aspartate aminotransferase, blood urea nitrogen, albumin, and creatine kinase levels did not differ between mice treated with the control vehicle and the mice treated with either AAV9/JeT-SLC6A1 or AAV9/MeP-SLC6A1 at either the high or low doses. Total bilirubin was significantly lower in both high-dose groups, although there is no known pathology associated with low total bilirubin.

The results of this experiment demonstrate that the rAAV viral vectors exhibit low toxicity and therefore can be used safely in a clinical setting.

What is claimed is:

1. A recombinant adeno-associated virus (rAAV) vector comprising in 5' to 3' direction:

(a) a first AAV inverted terminal repeat (ITR) sequence;
(b) a promoter sequence;
(c) a transgene nucleic acid molecule of SEQ ID NO: 3 or SEQ ID NO: 6
(d) a polyA sequence; and
(e) a second AAV ITR sequence.

2. The rAAV vector of claim 1, wherein the first AAV ITR sequence comprises the nucleic acid sequence set forth in SEQ ID NO: 12.

3. The rAAV vector of claim 1, wherein the second AAV ITR sequence comprises the nucleic acid sequence set forth in SEQ ID NO: 13.

4. The rAAV vector of claim 1, wherein the promoter sequence comprises a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, EFla promoter, Ubc promoter, human β-actin promoter, TRE promoter, Ac5 promoter, Polyhedrin promoter, CaMKIIa promoter, Gal1 promoter, TEF1 promoter, GDS promoter, ADH1 promoter, Ubi promoter, or α-1-antitrypsin (hAAT) promoter.

5. The rAAV vector of claim 1, wherein the promoter sequence comprises the nucleic acid sequence set forth in SEQ ID NO: 14.

6. The rAAV vector of claim 1, wherein the promoter sequence comprises the nucleic acid sequence set forth in SEQ ID NO: 15.

7. The rAAV vector of claim 1, wherein the polyA sequence comprises the nucleic acid sequence set forth in SEQ ID NO: 16.

8. The rAAV vector of claim 1, comprising, in the 5' to 3' direction:

a) a first AAV ITR sequence comprising the nucleic acid sequence set forth in SEQ ID NO: 12;
b) a promoter sequence comprising the nucleic acid sequence set forth in SEQ ID NO: 14;
c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence set forth in SEQ ID NO: 3;
d) a polyA sequence comprising the nucleic acid sequence set forth in SEQ ID NO: 16; and
e) a second AAV ITR sequence comprising the nucleic acid sequence set forth in SEQ ID NO: 13.

9. The rAAV vector of claim 1, comprising, in the 5' to 3' direction:

a) a first AAV ITR sequence comprising the nucleic acid sequence set forth in SEQ ID NO: 12;
b) a promoter sequence comprising the nucleic acid sequence set forth in SEQ ID NO: 15;
c) a transgene nucleic acid molecule, wherein the transgene nucleic acid molecule comprises a nucleic acid sequence encoding for a GAT1 polypeptide, wherein the nucleic acid sequence encoding for a GAT1 polypeptide comprises the nucleic acid sequence set forth in SEQ ID NO: 3;
d) a polyA sequence comprising the nucleic acid sequence set forth in SEQ ID NO: 16; and
e) a second AAV ITR sequence comprising the nucleic acid sequence set forth in SEQ ID NO: 13.

10. The rAAV vector of claim 1, wherein the rAAV vector comprises the nucleic acid sequence set forth in SEQ ID NO: 20.

11. The rAAV vector of claim 1, wherein the rAAV vector comprises the nucleic acid sequence set forth in SEQ ID NO: 22.

12. An rAAV viral vector comprising (i) an AAV capsid protein; and
(ii) an rAAV vector of claim 1.

13. The rAAV viral vector of claim 12, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

14. The rAAV viral vector of claim 12, wherein the AAV capsid protein is an AAV9 capsid protein.

15. A pharmaceutical composition comprising:

a) the rAAV viral vector of claim 12; and at least one pharmaceutically acceptable excipient and/or additive.

16. A method for treating a subject having a disease and/or disorder involving a SLC6A1 gene, the method comprising administering to the subject at least one therapeutically effective amount of the rAAV viral vector of claim 12.

17. The method of claim 16, wherein the disease and/or disorder involving the SLC6A1 gene is SLC6A1 haploinsufficiency or Doose Syndrome.

18. The method of claim 16, wherein the rAAV viral vector is administered to the subject at a dose ranging from about $10^{11}$ to about $10^{18}$ viral vector particles.

19. The method of claim 18, wherein the rAAV viral vector is administered to the subject at a dose ranging from about $10^{13}$ to about $10^{16}$ viral vector particles.

20. The method of claim 16, wherein the rAAV viral vector is administered to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve.

21. The method of claim 20, wherein the rAAV viral vector is administered intrathecally.

* * * * *

SEQUENCE LISTING

<160> NUMBER OF SEQ ID NOS: 24

<210> SEQ ID NO 1
<211> LENGTH: 598
<212> TYPE: PRT
<213> ORGANISM: Homo sapiens

<400> SEQUENCE: 1

```
Ala Thr Asn Gly Ser Lys Val Ala Asp Gly Gln Ile Ser Thr Glu Val
1               5                   10                  15

Ser Glu Ala Pro Val Ala Asn Asp Lys Pro Lys Thr Leu Val Val Lys
            20                  25                  30

Val Gln Lys Lys Ala Ala Asp Leu Pro Asp Arg Asp Thr Trp Lys Gly
        35                  40                  45

Arg Phe Asp Phe Leu Met Ser Cys Val Gly Tyr Ala Ile Gly Leu Gly
    50                  55                  60

Asn Val Trp Arg Phe Pro Tyr Leu Cys Gly Lys Asn Gly Gly Gly Ala
65                  70                  75                  80

Phe Leu Ile Pro Tyr Phe Leu Thr Leu Ile Phe Ala Gly Val Pro Leu
                85                  90                  95

Phe Leu Leu Glu Cys Ser Leu Gly Gln Tyr Thr Ser Ile Gly Gly Leu
            100                 105                 110

Gly Val Trp Lys Leu Ala Pro Met Phe Lys Gly Val Gly Leu Ala Ala
        115                 120                 125

Ala Val Leu Ser Phe Trp Leu Asn Ile Tyr Tyr Ile Val Ile Ile Ser
    130                 135                 140

Trp Ala Ile Tyr Tyr Leu Tyr Asn Ser Phe Thr Thr Thr Leu Pro Trp
145                 150                 155                 160

Lys Gln Cys Asp Asn Pro Trp Asn Thr Asp Arg Cys Phe Ser Asn Tyr
                165                 170                 175

Ser Met Val Asn Thr Thr Asn Met Thr Ser Ala Val Val Glu Phe Trp
            180                 185                 190

Glu Arg Asn Met His Gln Met Thr Asp Gly Leu Asp Lys Pro Gly Gln
        195                 200                 205

Ile Arg Trp Pro Leu Ala Ile Thr Leu Ala Ile Ala Trp Ile Leu Val
    210                 215                 220

Tyr Phe Cys Ile Trp Lys Gly Val Gly Trp Thr Gly Lys Val Val Tyr
225                 230                 235                 240

Phe Ser Ala Thr Tyr Pro Tyr Ile Met Leu Ile Ile Leu Phe Phe Arg
                245                 250                 255

Gly Val Thr Leu Pro Gly Ala Lys Glu Gly Ile Leu Phe Tyr Ile Thr
            260                 265                 270

Pro Asn Phe Arg Lys Leu Ser Asp Ser Glu Val Trp Leu Asp Ala Ala
        275                 280                 285

Thr Gln Ile Phe Phe Ser Tyr Gly Leu Gly Leu Gly Ser Leu Ile Ala
    290                 295                 300

Leu Gly Ser Tyr Asn Ser Phe His Asn Asn Val Tyr Arg Asp Ser Ile
305                 310                 315                 320

Ile Val Cys Cys Ile Asn Ser Cys Thr Ser Met Phe Ala Gly Phe Val
                325                 330                 335

Ile Phe Ser Ile Val Gly Phe Met Ala His Val Thr Lys Arg Ser Ile
            340                 345                 350

Ala Asp Val Ala Ala Ser Gly Pro Gly Leu Ala Phe Leu Ala Tyr Pro
        355                 360                 365
```

```
Glu Ala Val Thr Gln Leu Pro Ile Ser Pro Leu Trp Ala Ile Leu Phe
    370                 375                 380

Phe Ser Met Leu Leu Met Leu Gly Ile Asp Ser Gln Phe Cys Thr Val
385                 390                 395                 400

Glu Gly Phe Ile Thr Ala Leu Val Asp Glu Tyr Pro Arg Leu Leu Arg
                405                 410                 415

Asn Arg Arg Glu Leu Phe Ile Ala Ala Val Cys Ile Ile Ser Tyr Leu
            420                 425                 430

Ile Gly Leu Ser Asn Ile Thr Gln Gly Gly Ile Tyr Val Phe Lys Leu
        435                 440                 445

Phe Asp Tyr Tyr Ser Ala Ser Gly Met Ser Leu Leu Phe Leu Val Phe
    450                 455                 460

Phe Glu Cys Val Ser Ile Ser Trp Phe Tyr Gly Val Asn Arg Phe Tyr
465                 470                 475                 480

Asp Asn Ile Gln Glu Met Val Gly Ser Arg Pro Cys Ile Trp Trp Lys
                485                 490                 495

Leu Cys Trp Ser Phe Phe Thr Pro Ile Ile Val Ala Gly Val Phe Ile
            500                 505                 510

Phe Ser Ala Val Gln Met Thr Pro Leu Thr Met Gly Asn Tyr Val Phe
        515                 520                 525

Pro Lys Trp Gly Gln Gly Val Gly Trp Leu Met Ala Leu Ser Ser Met
    530                 535                 540

Val Leu Ile Pro Gly Tyr Met Ala Tyr Met Phe Leu Thr Leu Lys Gly
545                 550                 555                 560

Ser Leu Lys Gln Arg Ile Gln Val Met Val Gln Pro Ser Glu Asp Ile
                565                 570                 575

Val Arg Pro Glu Asn Gly Pro Glu Gln Pro Gln Ala Gly Ser Ser Thr
            580                 585                 590

Ser Lys Glu Ala Tyr Ile
        595


<210> SEQ ID NO 2
<211> LENGTH: 599
<212> TYPE: PRT
<213> ORGANISM: Homo sapiens

<400> SEQUENCE: 2

Met Ala Thr Asn Gly Ser Lys Val Ala Asp Gly Gln Ile Ser Thr Glu
1               5                   10                  15

Val Ser Glu Ala Pro Val Ala Asn Asp Lys Pro Lys Thr Leu Val Val
            20                  25                  30

Lys Val Gln Lys Lys Ala Ala Asp Leu Pro Asp Arg Asp Thr Trp Lys
        35                  40                  45

Gly Arg Phe Asp Phe Leu Met Ser Cys Val Gly Tyr Ala Ile Gly Leu
    50                  55                  60

Gly Asn Val Trp Arg Phe Pro Tyr Leu Cys Gly Lys Asn Gly Gly Gly
65                  70                  75                  80

Ala Phe Leu Ile Pro Tyr Phe Leu Thr Leu Ile Phe Ala Gly Val Pro
                85                  90                  95

Leu Phe Leu Leu Glu Cys Ser Leu Gly Gln Tyr Thr Ser Ile Gly Gly
            100                 105                 110

Leu Gly Val Trp Lys Leu Ala Pro Met Phe Lys Gly Val Gly Leu Ala
        115                 120                 125

Ala Ala Val Leu Ser Phe Trp Leu Asn Ile Tyr Tyr Ile Val Ile Ile
    130                 135                 140
```

-continued

```
Ser Trp Ala Ile Tyr Tyr Leu Tyr Asn Ser Phe Thr Thr Thr Leu Pro
145                 150                 155                 160

Trp Lys Gln Cys Asp Asn Pro Trp Asn Thr Asp Arg Cys Phe Ser Asn
                165                 170                 175

Tyr Ser Met Val Asn Thr Thr Asn Met Thr Ser Ala Val Val Glu Phe
            180                 185                 190

Trp Glu Arg Asn Met His Gln Met Thr Asp Gly Leu Asp Lys Pro Gly
        195                 200                 205

Gln Ile Arg Trp Pro Leu Ala Ile Thr Leu Ala Ile Ala Trp Ile Leu
    210                 215                 220

Val Tyr Phe Cys Ile Trp Lys Gly Val Gly Trp Thr Gly Lys Val Val
225                 230                 235                 240

Tyr Phe Ser Ala Thr Tyr Pro Tyr Ile Met Leu Ile Ile Leu Phe Phe
                245                 250                 255

Arg Gly Val Thr Leu Pro Gly Ala Lys Glu Gly Ile Leu Phe Tyr Ile
            260                 265                 270

Thr Pro Asn Phe Arg Lys Leu Ser Asp Ser Glu Val Trp Leu Asp Ala
        275                 280                 285

Ala Thr Gln Ile Phe Phe Ser Tyr Gly Leu Gly Leu Gly Ser Leu Ile
    290                 295                 300

Ala Leu Gly Ser Tyr Asn Ser Phe His Asn Asn Val Tyr Arg Asp Ser
305                 310                 315                 320

Ile Ile Val Cys Cys Ile Asn Ser Cys Thr Ser Met Phe Ala Gly Phe
                325                 330                 335

Val Ile Phe Ser Ile Val Gly Phe Met Ala His Val Thr Lys Arg Ser
            340                 345                 350

Ile Ala Asp Val Ala Ala Ser Gly Pro Gly Leu Ala Phe Leu Ala Tyr
        355                 360                 365

Pro Glu Ala Val Thr Gln Leu Pro Ile Ser Pro Leu Trp Ala Ile Leu
    370                 375                 380

Phe Phe Ser Met Leu Leu Met Leu Gly Ile Asp Ser Gln Phe Cys Thr
385                 390                 395                 400

Val Glu Gly Phe Ile Thr Ala Leu Val Asp Glu Tyr Pro Arg Leu Leu
                405                 410                 415

Arg Asn Arg Arg Glu Leu Phe Ile Ala Ala Val Cys Ile Ile Ser Tyr
            420                 425                 430

Leu Ile Gly Leu Ser Asn Ile Thr Gln Gly Gly Ile Tyr Val Phe Lys
        435                 440                 445

Leu Phe Asp Tyr Tyr Ser Ala Ser Gly Met Ser Leu Leu Phe Leu Val
    450                 455                 460

Phe Phe Glu Cys Val Ser Ile Ser Trp Phe Tyr Gly Val Asn Arg Phe
465                 470                 475                 480

Tyr Asp Asn Ile Gln Glu Met Val Gly Ser Arg Pro Cys Ile Trp Trp
                485                 490                 495

Lys Leu Cys Trp Ser Phe Phe Thr Pro Ile Ile Val Ala Gly Val Phe
            500                 505                 510

Ile Phe Ser Ala Val Gln Met Thr Pro Leu Thr Met Gly Asn Tyr Val
        515                 520                 525

Phe Pro Lys Trp Gly Gln Gly Val Gly Trp Leu Met Ala Leu Ser Ser
    530                 535                 540

Met Val Leu Ile Pro Gly Tyr Met Ala Tyr Met Phe Leu Thr Leu Lys
545                 550                 555                 560
```

-continued

```
Gly Ser Leu Lys Gln Arg Ile Gln Val Met Val Gln Pro Ser Glu Asp
                565                 570                 575

Ile Val Arg Pro Glu Asn Gly Pro Glu Gln Pro Gln Ala Gly Ser Ser
            580                 585                 590

Thr Ser Lys Glu Ala Tyr Ile
        595


<210> SEQ ID NO 3
<211> LENGTH: 1794
<212> TYPE: DNA
<213> ORGANISM: Homo sapiens

<400> SEQUENCE: 3

gcgaccaacg gtagcaaggt cgcagacggc cagatcagca ccgaggtgtc cgaagcccct     60

gtggcgaacg ataagcccaa gaccctggtg gtcaaggtcc agaagaaggc agcagacttg    120

ccggatcgcg acacttggaa gggtcgcttc gacttcctga tgtcgtgcgt gggctacgcc    180

attggactgg gaaacgtctg gaggttcccg tacctttgtg ggaaaaatgg gggtggagcc    240

tttctgattc cctacttcct tactctgatt ttcgccggag tgcctctgtt tctactggag    300

tgcagcttgg ggcagtacac gtccatcgga gggctcggag tgtggaagct ggcgccgatg    360

ttcaagggcg tgggcttggc tgctgccgtg ctgagcttct ggctgaatat ctactacatc    420

gtgatcatct cgtgggccat ctactatctt tacaactcct tcaccactac tctgccctgg    480

aaacagtgcg acaacccctg gaataccgac cggtgcttct ctaactactc gatggtcaac    540

accactaaca tgaccagcgc cgtggtcgag ttctgggaga ggaacatgca tcaaatgaca    600

gacggcctcg acaagcccgg acagattcgg tggccactgg ccattaccct cgcgattgca    660

tggatcttgg tgtacttctg catctggaag ggagtgggct ggactggaaa ggtcgtgtac    720

ttctcggcca cctacccgta cattatgctg atcattctgt tttccggggg cgtgactctg    780

cccggagcca aggaaggcat cctgttctac attactccta actttcggaa gctgtcggac    840

tcagaagtct ggctggacgc agctacccag atcttctttt cctacggact gggtctgggc    900

tccctgatcg ccctgggctc ctataactcc ttccacaaca acgtgtatcg cgactccatc    960

atcgtgtgtt gcatcaactc ctgcacctca atgttcgccg gcttcgtgat cttcagcatt   1020

gtgggcttca tggcccacgt gaccaagcgc agtatcgccg atgtggctgc gtccggacct   1080

ggactggcgt tcctcgcgta cccggaagcc gtgacccagc tcccgatctc gccgttgtgg   1140

gcgattctct tcttctccat gcttctgatg ctgggaatag actcccagtt ctgtaccgtg   1200

gaagggttta tcactgccct ggtggacgag taccctagac tgctccggaa ccggagagaa   1260

ctgttcatcg ctgccgtgtg catcatttca tacctcatcg gcctcagcaa catcacccag   1320

ggtggaatct acgtgttcaa gctgttcgac tactattcgg cctccggaat gtccctgctg   1380

ttcctggtgt tcttcgaatg cgtgtccatc tcctggttct acggcgtcaa ccggttctac   1440

gataacattc aggaaatggt cggatcacgc ccctgcattt ggtggaagct ctgctggtcc   1500

ttcttcaccc cgatcatcgt ggccggagtg ttcatcttta gcgctgtgca gatgactccc   1560

ctgactatgg ggaactacgt gttcccgaaa tggggtcaag gagtggggtg gctgatggcg   1620

ctcagcagca tggtgctgat ccctggctac atggcctaca tgtttctgac cctgaaggga   1680

tcactgaagc agcgcatcca agtcatggtg caaccctccg aagatatcgt cagaccagaa   1740

aacggacctg agcagccaca ggccggttcc tcgacctcca aagaggccta catc         1794


<210> SEQ ID NO 4
```

-continued

<211> LENGTH: 1797
<212> TYPE: DNA
<213> ORGANISM: Homo sapiens

<400> SEQUENCE: 4
gcgaccaacg gtagcaaggt cgcagacggc cagatcagca ccgaggtgtc cgaagcccct 60
gtggcgaacg ataagcccaa gaccctggtg gtcaaggtcc agaagaaggc agcagacttg 120
ccggatcgcg acacttggaa gggtcgcttc gacttcctga tgtcgtgcgt gggctacgcc 180
attggactgg gaaacgtctg gaggttcccg tacctttgtg ggaaaaatgg gggtggagcc 240
tttctgattc cctacttcct tactctgatt ttcgccggag tgcctctgtt tctactggag 300
tgcagcttgg ggcagtacac gtccatcgga gggctcggag tgtggaagct ggcgccgatg 360
ttcaagggcg tgggcttggc tgctgccgtg ctgagcttct ggctgaatat ctactacatc 420
gtgatcatct cgtgggccat ctactatctt tacaactcct tcaccactac tctgccctgg 480
aaacagtgcg acaacccctg gaataccgac cggtgcttct ctaactactc gatggtcaac 540
accactaaca tgaccagcgc cgtggtcgag ttctgggaga ggaacatgca tcaaatgaca 600
gacggcctcg acaagcccgg acagattcgg tggccactgg ccattaccct cgcgattgca 660
tggatcttgg tgtacttctg catctggaag ggagtgggct ggactggaaa ggtcgtgtac 720
ttctcggcca cctacccgta cattatgctg atcattctgt tttccggggg cgtgactctg 780
cccggagcca aggaaggcat cctgttctac attactccta actttcggaa gctgtcggac 840
tcagaagtct ggctggacgc agctacccag atcttctttt cctacggact gggtctgggc 900
tccctgatcg ccctgggctc ctataactcc ttccacaaca acgtgtatcg cgactccatc 960
atcgtgtgtt gcatcaactc ctgcacctca atgttcgccg gcttcgtgat cttcagcatt 1020
gtgggcttca tggcccacgt gaccaagcgc agtatcgccg atgtggctgc gtccggacct 1080
ggactggcgt tcctcgcgta cccggaagcc gtgacccagc tcccgatctc gccgttgtgg 1140
gcgattctct tcttctccat gcttctgatg ctgggaatag actcccagtt ctgtaccgtg 1200
gaagggttta tcactgccct ggtggacgag taccctagac tgctccggaa ccggagagaa 1260
ctgttcatcg ctgccgtgtg catcatttca tacctcatcg gcctcagcaa catcacccag 1320
ggtggaatct acgtgttcaa gctgttcgac tactattcgg cctccggaat gtccctgctg 1380
ttcctggtgt tcttcgaatg cgtgtccatc tcctggttct acggcgtcaa ccggttctac 1440
gataacattc aggaaatggt cggatcacgc ccctgcattt ggtggaagct ctgctggtcc 1500
ttcttcaccc cgatcatcgt ggccggagtg ttcatcttta gcgctgtgca gatgactccc 1560
ctgactatgg ggaactacgt gttcccgaaa tggggtcaag gagtggggtg gctgatggcg 1620
ctcagcagca tggtgctgat ccctggctac atggcctaca tgtttctgac cctgaaggga 1680
tcactgaagc agcgcatcca agtcatggtg caaccctccg aagatatcgt cagaccagaa 1740
aacggacctg agcagccaca ggccggttcc tcgacctcca aagaggccta catctaa 1797

<210> SEQ ID NO 5
<211> LENGTH: 1800
<212> TYPE: DNA
<213> ORGANISM: Homo sapiens

<400> SEQUENCE: 5
gcgaccaacg gtagcaaggt cgcagacggc cagatcagca ccgaggtgtc cgaagcccct 60
gtggcgaacg ataagcccaa gaccctggtg gtcaaggtcc agaagaaggc agcagacttg 120
ccggatcgcg acacttggaa gggtcgcttc gacttcctga tgtcgtgcgt gggctacgcc 180

-continued

```
attggactgg gaaacgtctg gaggttcccg tacctttgtg ggaaaaatgg gggtggagcc    240
tttctgattc cctacttcct tactctgatt ttcgccggag tgcctctgtt tctactggag    300
tgcagcttgg ggcagtacac gtccatcgga gggctcggag tgtggaagct ggcgccgatg    360
ttcaagggcg tgggcttggc tgctgccgtg ctgagcttct ggctgaatat ctactacatc    420
gtgatcatct cgtgggccat ctactatctt tacaactcct tcaccactac tctgccctgg    480
aaacagtgcg acaaccccctg gaataccgac cggtgcttct ctaactactc gatggtcaac    540
accactaaca tgaccagcgc cgtggtcgag ttctgggaga ggaacatgca tcaaatgaca    600
gacggcctcg acaagcccgg acagattcgg tggccactgg ccattaccct cgcgattgca    660
tggatcttgg tgtacttctg catctggaag ggagtgggct ggactggaaa ggtcgtgtac    720
ttctcggcca cctacccgta cattatgctg atcattctgt ttttccgggg cgtgactctg    780
cccggagcca aggaaggcat cctgttctac attactccta actttcggaa gctgtcggac    840
tcagaagtct ggctggacgc agctacccag atcttctttt cctacggact gggtctgggc    900
tccctgatcg ccctgggctc ctataactcc ttccacaaca acgtgtatcg cgactccatc    960
atcgtgtgtt gcatcaactc ctgcacctca atgttcgccg gcttcgtgat cttcagcatt   1020
gtgggcttca tggcccacgt gaccaagcgc agtatcgccg atgtggctgc gtccggacct   1080
ggactggcgt tcctcgcgta cccggaagcc gtgacccagc tcccgatctc gccgttgtgg   1140
gcgattctct tcttctccat gcttctgatg ctgggaatag actcccagtt ctgtaccgtg   1200
gaagggttta tcactgccct ggtggacgag taccctagac tgctccggaa ccggagagaa   1260
ctgttcatcg ctgccgtgtg catcatttca tacctcatcg gcctcagcaa catcacccag   1320
ggtggaatct acgtgttcaa gctgttcgac tactattcgg cctccggaat gtccctgctg   1380
ttcctggtgt tcttcgaatg cgtgtccatc tcctggttct acggcgtcaa ccggttctac   1440
gataacattc aggaaatggt cggatcacgc ccctgcattt ggtggaagct ctgctggtcc   1500
ttcttcaccc cgatcatcgt ggccggagtg ttcatcttta gcgctgtgca gatgactccc   1560
ctgactatgg ggaactacgt gttcccgaaa tggggtcaag gagtggggtg gctgatggcg   1620
ctcagcagca tggtgctgat ccctggctac atggcctaca tgtttctgac cctgaaggga   1680
tcactgaagc agcgcatcca agtcatggtg caaccctccg aagatatcgt cagaccagaa   1740
aacggacctg agcagccaca ggccggttcc tcgacctcca aagaggccta catctaataa   1800
```

<210> SEQ ID NO 6
<211> LENGTH: 1801
<212> TYPE: DNA
<213> ORGANISM: Homo sapiens

<400> SEQUENCE: 6

```
gcgaccaacg gtagcaaggt cgcagacggc cagatcagca ccgaggtgtc cgaagcccct     60
gtggcgaacg ataagcccaa gaccctggtg gtcaaggtcc agaagaaggc agcagacttg    120
ccggatcgcg acacttggaa gggtcgcttc gacttcctga tgtcgtgcgt gggctacgcc    180
attggactgg gaaacgtctg gaggttcccg tacctttgtg ggaaaaatgg gggtggagcc    240
tttctgattc cctacttcct tactctgatt ttcgccggag tgcctctgtt tctactggag    300
tgcagcttgg ggcagtacac gtccatcgga gggctcggag tgtggaagct ggcgccgatg    360
ttcaagggcg tgggcttggc tgctgccgtg ctgagcttct ggctgaatat ctactacatc    420
gtgatcatct cgtgggccat ctactatctt tacaactcct tcaccactac tctgccctgg    480
```

-continued

```
aaacagtgcg acaaccccctg gaataccgac cggtgcttct ctaactactc gatggtcaac    540
accactaaca tgaccagcgc cgtggtcgag ttctgggaga ggaacatgca tcaaatgaca    600
gacggcctcg acaagcccgg acagattcgg tggccactgg ccattaccct cgcgattgca    660
tggatcttgg tgtacttctg catctggaag ggagtgggct ggactggaaa ggtcgtgtac    720
ttctcggcca cctacccgta cattatgctg atcattctgt tttccgggg cgtgactctg    780
cccggagcca aggaaggcat cctgttctac attactccta actttcggaa gctgtcggac    840
tcagaagtct ggctggacgc agctacccag atcttctttt cctacggact gggtctgggc    900
tccctgatcg ccctgggctc ctataactcc ttccacaaca acgtgtatcg cgactccatc    960
atcgtgtgtt gcatcaactc ctgcacctca atgttcgccg gcttcgtgat cttcagcatt   1020
gtgggcttca tggcccacgt gaccaagcgc agtatcgccg atgtggctgc gtccggacct   1080
ggactggcgt tcctcgcgta cccggaagcc gtgacccagc tcccgatctc gccgttgtgg   1140
gcgattctct tcttctccat gcttctgatg ctgggaatag actcccagtt ctgtaccgtg   1200
gaagggttta tcactgccct ggtggacgag taccctagac tgctccggaa ccggagagaa   1260
ctgttcatcg ctgccgtgtg catcatttca tacctcatcg gcctcagcaa catcacccag   1320
ggtggaatct acgtgttcaa gctgttcgac tactattcgg cctccggaat gtccctgctg   1380
ttcctggtgt tcttcgaatg cgtgtccatc tcctggttct acggcgtcaa ccggttctac   1440
gataacattc aggaaatggt cggatcacgc ccctgcattt ggtggaagct ctgctggtcc   1500
ttcttcaccc cgatcatcgt ggccggagtg ttcatcttta gcgctgtgca gatgactccc   1560
ctgactatgg ggaactacgt gttcccgaaa tggggtcaag gagtggggtg gctgatggcg   1620
ctcagcagca tggtgctgat ccctggctac atggcctaca tgtttctgac cctgaaggga   1680
tcactgaagc agcgcatcca agtcatggtg caaccctccg aagatatcgt cagaccagaa   1740
aacggacctg agcagccaca ggccggttcc tcgacctcca aagaggccta catctaataa   1800
t                                                                   1801
```

<210> SEQ ID NO 7
<211> LENGTH: 1797
<212> TYPE: DNA
<213> ORGANISM: Homo sapiens

<400> SEQUENCE: 7

```
atggcgacca acggtagcaa ggtcgcagac ggccagatca gcaccgaggt gtccgaagcc     60
cctgtggcga acgataagcc caagaccctg gtggtcaagg tccagaagaa ggcagcagac    120
ttgccggatc gcgacacttg gaagggtcgc ttcgacttcc tgatgtcgtg cgtgggctac    180
gccattggac tgggaaacgt ctggaggttc ccgtaccttt gtgggaaaaa tgggggtgga    240
gcctttctga ttccctactt ccttactctg attttcgccg gagtgcctct gtttctactg    300
gagtgcagct tggggcagta cacgtccatc ggagggctcg gagtgtggaa gctggcgccg    360
atgttcaagg gcgtgggctt ggctgctgcc gtgctgagct tctggctgaa tatctactac    420
atcgtgatca tctcgtgggc catctactat ctttacaact ccttcaccac tactctgccc    480
tggaaacagt gcgacaaccc ctggaatacc gaccggtgct tctctaacta ctcgatggtc    540
aacaccacta acatgaccag cgccgtggtc gagttctggg agaggaacat gcatcaaatg    600
acagacggcc tcgacaagcc cggacagatt cggtggccac tggccattac cctcgcgatt    660
gcatggatct tggtgtactt ctgcatctgg aagggagtgg gctggactgg aaaggtcgtg    720
tacttctcgg ccacctaccc gtacattatg ctgatcattc tgtttttccg ggcgtgact     780
```

ctgcccggag ccaaggaagg catcctgttc tacattactc ctaactttcg gaagctgtcg 840
gactcagaag tctggctgga cgcagctacc cagatcttct tttcctacgg actgggtctg 900
ggctccctga tcgccctggg ctcctataac tccttccaca acaacgtgta tcgcgactcc 960
atcatcgtgt gttgcatcaa ctcctgcacc tcaatgttcg ccggcttcgt gatcttcagc 1020
attgtgggct tcatggccca cgtgaccaag cgcagtatcg ccgatgtggc tgcgtccgga 1080
cctggactgg cgttcctcgc gtacccggaa gccgtgaccc agctcccgat ctcgccgttg 1140
tgggcgattc tcttcttctc catgcttctg atgctgggaa tagactccca gttctgtacc 1200
gtggaagggt ttatcactgc cctggtggac gagtacccta gactgctccg gaaccggaga 1260
gaactgttca tcgctgccgt gtgcatcatt tcatacctca tcggcctcag caacatcacc 1320
cagggtggaa tctacgtgtt caagctgttc gactactatt cggcctccgg aatgtccctg 1380
ctgttcctgg tgttcttcga atgcgtgtcc atctcctggt tctacggcgt caaccggttc 1440
tacgataaca ttcaggaaat ggtcggatca cgcccctgca tttggtggaa gctctgctgg 1500
tccttcttca ccccgatcat cgtggccgga gtgttcatct ttagcgctgt gcagatgact 1560
cccctgacta tggggaacta cgtgttcccg aaatggggtc aaggagtggg gtggctgatg 1620
gcgctcagca gcatggtgct gatccctggc tacatggcct acatgtttct gaccctgaag 1680
ggatcactga agcagcgcat ccaagtcatg gtgcaaccct ccgaagatat cgtcagacca 1740
gaaaacggac ctgagcagcc acaggccggt tcctcgacct ccaaagaggc ctacatc 1797

<210> SEQ ID NO 8
<211> LENGTH: 1800
<212> TYPE: DNA
<213> ORGANISM: Homo sapiens

<400> SEQUENCE: 8
atggcgacca acggtagcaa ggtcgcagac ggccagatca gcaccgaggt gtccgaagcc 60
cctgtggcga acgataagcc caagaccctg gtggtcaagg tccagaagaa ggcagcagac 120
ttgccggatc gcgacacttg gaagggtcgc ttcgacttcc tgatgtcgtg cgtgggctac 180
gccattggac tgggaaacgt ctggaggttc ccgtaccttt gtgggaaaaa tgggggtgga 240
gcctttctga ttccctactt ccttactctg attttcgccg gagtgcctct gtttctactg 300
gagtgcagct tggggcagta cacgtccatc ggagggctcg gagtgtggaa gctggcgccg 360
atgttcaagg gcgtgggctt ggctgctgcc gtgctgagct tctggctgaa tatctactac 420
atcgtgatca tctcgtgggc catctactat ctttacaact ccttcaccac tactctgccc 480
tggaaacagt gcgacaaccc ctggaatacc gaccggtgct tctctaacta ctcgatggtc 540
aacaccacta acatgaccag cgccgtggtc gagttctggg agaggaacat gcatcaaatg 600
acagacggcc tcgacaagcc cggacagatt cggtggccac tggccattac cctcgcgatt 660
gcatggatct tggtgtactt ctgcatctgg aagggagtgg gctggactgg aaaggtcgtg 720
tacttctcgg ccacctaccc gtacattatg ctgatcattc tgtttttccg gggcgtgact 780
ctgcccggag ccaaggaagg catcctgttc tacattactc ctaactttcg gaagctgtcg 840
gactcagaag tctggctgga cgcagctacc cagatcttct tttcctacgg actgggtctg 900
ggctccctga tcgccctggg ctcctataac tccttccaca acaacgtgta tcgcgactcc 960
atcatcgtgt gttgcatcaa ctcctgcacc tcaatgttcg ccggcttcgt gatcttcagc 1020
attgtgggct tcatggccca cgtgaccaag cgcagtatcg ccgatgtggc tgcgtccgga 1080

-continued cctggactgg cgttcctcgc gtacccggaa gccgtgaccc agctcccgat ctcgccgttg 1140
tgggcgattc tcttcttctc catgcttctg atgctgggaa tagactccca gttctgtacc 1200
gtggaagggt ttatcactgc cctggtggac gagtacccta gactgctccg gaaccggaga 1260
gaactgttca tcgctgccgt gtgcatcatt tcatacctca tcggcctcag caacatcacc 1320
cagggtggaa tctacgtgtt caagctgttc gactactatt cggcctccgg aatgtccctg 1380
ctgttcctgg tgttcttcga atgcgtgtcc atctcctggt tctacggcgt caaccggttc 1440
tacgataaca ttcaggaaat ggtcggatca cgcccctgca tttggtggaa gctctgctgg 1500
tccttcttca ccccgatcat cgtggccgga gtgttcatct ttagcgctgt gcagatgact 1560
cccctgacta tggggaacta cgtgttcccg aaatggggtc aaggagtggg gtggctgatg 1620
gcgctcagca gcatggtgct gatccctggc tacatggcct acatgtttct gaccctgaag 1680
ggatcactga agcagcgcat ccaagtcatg gtgcaaccct ccgaagatat cgtcagacca 1740
gaaaacggac ctgagcagcc acaggccggt tcctcgacct ccaaagaggc ctacatctaa 1800

<210> SEQ ID NO 9
<211> LENGTH: 1803
<212> TYPE: DNA
<213> ORGANISM: Homo sapiens

<400> SEQUENCE: 9
atggcgacca acggtagcaa ggtcgcagac ggccagatca gcaccgaggt gtccgaagcc 60
cctgtggcga acgataagcc caagaccctg gtggtcaagg tccagaagaa ggcagcagac 120
ttgccggatc gcgacacttg gaagggtcgc ttcgacttcc tgatgtcgtg cgtgggctac 180
gccattggac tgggaaacgt ctggaggttc ccgtaccttt gtgggaaaaa tgggggtgga 240
gcctttctga ttccctactt ccttactctg attttcgccg gagtgcctct gtttctactg 300
gagtgcagct tggggcagta cacgtccatc ggagggctcg gagtgtggaa gctggcgccg 360
atgttcaagg gcgtgggctt ggctgctgcc gtgctgagct tctggctgaa tatctactac 420
atcgtgatca tctcgtgggc catctactat ctttacaact ccttcaccac tactctgccc 480
tggaaacagt gcgacaaccc ctggaatacc gaccggtgct tctctaacta ctcgatggtc 540
aacaccacta acatgaccag cgccgtggtc gagttctggg agaggaacat gcatcaaatg 600
acagacggcc tcgacaagcc cggacagatt cggtggccac tggccattac cctcgcgatt 660
gcatggatct tggtgtactt ctgcatctgg aagggagtgg gctggactgg aaaggtcgtg 720
tacttctcgg ccacctaccc gtacattatg ctgatcattc tgtttttccg ggcgtgact 780 ctgcccggag ccaaggaagg catcctgttc tacattactc ctaactttcg gaagctgtcg 840
gactcagaag tctggctgga cgcagctacc cagatcttct tttcctacgg actgggtctg 900
ggctccctga tcgccctggg ctcctataac tccttccaca acaacgtgta tcgcgactcc 960
atcatcgtgt gttgcatcaa ctcctgcacc tcaatgttcg ccggcttcgt gatcttcagc 1020
attgtgggct tcatggccca cgtgaccaag cgcagtatcg ccgatgtggc tgcgtccgga 1080
cctggactgg cgttcctcgc gtacccggaa gccgtgaccc agctcccgat ctcgccgttg 1140
tgggcgattc tcttcttctc catgcttctg atgctgggaa tagactccca gttctgtacc 1200
gtggaagggt ttatcactgc cctggtggac gagtacccta gactgctccg gaaccggaga 1260
gaactgttca tcgctgccgt gtgcatcatt tcatacctca tcggcctcag caacatcacc 1320
cagggtggaa tctacgtgtt caagctgttc gactactatt cggcctccgg aatgtccctg 1380
ctgttcctgg tgttcttcga atgcgtgtcc atctcctggt tctacggcgt caaccggttc 1440

-continued tacgataaca ttcaggaaat ggtcggatca cgcccctgca tttggtggaa gctctgctgg 1500
tccttcttca ccccgatcat cgtggccgga gtgttcatct ttagcgctgt gcagatgact 1560
cccctgacta tggggaacta cgtgttcccg aaatggggtc aaggagtggg gtggctgatg 1620
gcgctcagca gcatggtgct gatccctggc tacatggcct acatgtttct gaccctgaag 1680
ggatcactga agcagcgcat ccaagtcatg gtgcaaccct ccgaagatat cgtcagacca 1740
gaaaacggac ctgagcagcc acaggccggt tcctcgacct ccaaagaggc ctacatctaa 1800
taa 1803

<210> SEQ ID NO 10
<211> LENGTH: 1804
<212> TYPE: DNA
<213> ORGANISM: Homo sapiens

<400> SEQUENCE: 10
atggcgacca acggtagcaa ggtcgcagac ggccagatca gcaccgaggt gtccgaagcc 60
cctgtggcga acgataagcc caagaccctg gtggtcaagg tccagaagaa ggcagcagac 120
ttgccggatc gcgacacttg gaagggtcgc ttcgacttcc tgatgtcgtg cgtgggctac 180
gccattggac tgggaaacgt ctggaggttc ccgtaccttt gtgggaaaaa tgggggtgga 240
gcctttctga ttccctactt ccttactctg attttcgccg gagtgcctct gtttctactg 300
gagtgcagct tggggcagta cacgtccatc ggagggctcg gagtgtggaa gctggcgccg 360
atgttcaagg gcgtgggctt ggctgctgcc gtgctgagct tctggctgaa tatctactac 420
atcgtgatca tctcgtgggc catctactat ctttacaact ccttcaccac tactctgccc 480
tggaaacagt gcgacaaccc ctggaatacc gaccggtgct tctctaacta ctcgatggtc 540
aacaccacta acatgaccag cgccgtggtc gagttctggg agaggaacat gcatcaaatg 600
acagacggcc tcgacaagcc cggacagatt cggtggccac tggccattac cctcgcgatt 660
gcatggatct tggtgtactt ctgcatctgg aagggagtgg gctggactgg aaaggtcgtg 720
tacttctcgg ccacctaccc gtacattatg ctgatcattc tgtttttccg ggcgtgact 780 ctgcccggag ccaaggaagg catcctgttc tacattactc ctaactttcg gaagctgtcg 840
gactcagaag tctggctgga cgcagctacc cagatcttct tttcctacgg actgggtctg 900
ggctccctga tcgccctggg ctcctataac tccttccaca acaacgtgta tcgcgactcc 960
atcatcgtgt gttgcatcaa ctcctgcacc tcaatgttcg ccggcttcgt gatcttcagc 1020
attgtgggct tcatggccca cgtgaccaag cgcagtatcg ccgatgtggc tgcgtccgga 1080
cctggactgg cgttcctcgc gtacccggaa gccgtgaccc agctcccgat ctcgccgttg 1140
tgggcgattc tcttcttctc catgcttctg atgctgggaa tagactccca gttctgtacc 1200
gtggaagggt ttatcactgc cctggtggac gagtacccta gactgctccg gaaccggaga 1260
gaactgttca tcgctgccgt gtgcatcatt tcatacctca tcggcctcag caacatcacc 1320
cagggtggaa tctacgtgtt caagctgttc gactactatt cggcctccgg aatgtccctg 1380
ctgttcctgg tgttcttcga atgcgtgtcc atctcctggt tctacggcgt caaccggttc 1440
tacgataaca ttcaggaaat ggtcggatca cgcccctgca tttggtggaa gctctgctgg 1500
tccttcttca ccccgatcat cgtggccgga gtgttcatct ttagcgctgt gcagatgact 1560
cccctgacta tggggaacta cgtgttcccg aaatggggtc aaggagtggg gtggctgatg 1620
gcgctcagca gcatggtgct gatccctggc tacatggcct acatgtttct gaccctgaag 1680

-continued ggatcactga agcagcgcat ccaagtcatg gtgcaaccct ccgaagatat cgtcagacca 1740
gaaaacggac ctgagcagcc acaggccggt tcctcgacct ccaaagaggc ctacatctaa 1800
taat 1804

<210> SEQ ID NO 11
<211> LENGTH: 1797
<212> TYPE: DNA
<213> ORGANISM: Homo sapiens

<400> SEQUENCE: 11
atggcgacca acggcagcaa ggtggccgac gggcagatct ccaccgaggt cagcgaggcc 60
cctgtggcca atgacaagcc caaaaccttg gtggtcaagg tgcagaagaa ggcggcagac 120
ctccccgacc gggacacgtg gaagggccgc ttcgacttcc tcatgtcctg tgtgggctat 180
gccatcggcc tgggcaacgt ctggaggttc ccctatctct gcgggaaaaa tggtggggga 240
gccttcctga tcccctattt cctgacactc atctttgcgg gggtcccact cttcctgctg 300
gagtgctccc tgggccagta cacctccatc ggggggctag ggtatggaa gctggctcct 360 atgttcaagg gcgtgggcct tgcggctgct gtgctatcat tctggctgaa catctactac 420
atcgtcatca tctcctgggc catttactac ctgtacaact ccttcaccac gacactgccg 480
tggaaacagt gcgacaaccc ctggaacaca gaccgctgct tctccaacta cagcatggtc 540
aacactacca acatgaccag cgctgtggtg gagttctggg agcgcaacat gcatcagatg 600
acggacgggc tggataagcc aggtcagatc cgctggccac tggccatcac gctggccatc 660
gcctggatcc ttgtgtattt ctgtatctgg aagggtgttg gctggactgg aaaggtggtc 720
tacttttcag ccacataccc ctacatcatg ctgatcatcc tgttcttccg tggagtgacg 780
ctgcccgggg ccaaggaggg catcctcttc tacatcacac ccaacttccg caagctgtct 840
gactccgagg tgtggctgga tgcggcaacc cagatcttct tctcatacgg gctgggcctg 900
gggtccctga tcgctctcgg gagctacaac tctttccaca acaatgtcta cagggactcc 960
atcatcgtct gctgcatcaa ttcgtgcacc agcatgttcg caggattcgt catcttctcc 1020
atcgtgggct tcatggccca tgtcaccaag aggtccattg ctgatgtggc cgcctcaggc 1080
cccgggctgg cgttcctggc atacccagag gcggtgaccc agctgcctat ctccccactc 1140
tgggccatcc tcttcttctc catgctgttg atgctgggca ttgacagcca gttctgcact 1200
gtggagggct tcatcacagc cctggtggat gagtacccca ggctcctccg caaccgcaga 1260
gagctcttca ttgctgctgt ctgcatcatc tcctacctga tcggtctctc taacatcact 1320
caggggggta tttatgtctt caaactcttt gactactact ctgccagtgg catgagcctg 1380
ctgttcctcg tgttctttga atgtgtctct atttcctggt tttacggtgt caaccgattc 1440
tatgacaata tccaagagat ggttggatcc aggccctgca tctggtggaa actctgctgg 1500
tctttcttca caccaatcat tgtggcgggc gtgttcattt tcagtgctgt gcagatgacg 1560
ccactcacca tgggaaacta tgttttcccc aagtggggcc agggtgtggg ctggctgatg 1620
gctctgtctt ccatggtcct catccccggg tacatggcct acatgttcct cgccctaaag 1680
ggctccctga agcagcgcat ccaagtcatg gtccagccca gcgaagacac tgttcgccca 1740
gagaatggtc ctgagcacgc ccaggcgggc agctccacca gcaaggaggc ctacatc 1797

<210> SEQ ID NO 12
<211> LENGTH: 106
<212> TYPE: DNA
<213> ORGANISM: adeno-associated virus

<400> SEQUENCE: 12
ctgcgcgctc gctcgctcac tgaggccgcc cgggcaaagc ccgggcgtcg ggcgaccttt 60
ggtcgcccgg cctcagtgag cgagcgagcg cgcagagagg gagtgg 106

<210> SEQ ID NO 13
<211> LENGTH: 170
<212> TYPE: DNA
<213> ORGANISM: Adeno-Associated Virus

<400> SEQUENCE: 13
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcca gctggcgtaa tagcgaagag gcccgcaccg atcgcccttc 170

<210> SEQ ID NO 14
<211> LENGTH: 164
<212> TYPE: DNA
<213> ORGANISM: Artificial Sequence
<220> FEATURE:
<223> OTHER INFORMATION: JeT promoter

<400> SEQUENCE: 14
gggcggagtt agggcggagc caatcagcgt gcgccgttcc gaaagttgcc ttttatggct 60
gggcggagaa tgggcggtga acgccgatga ttatataagg acgcgccggg tgtggcacag 120
ctagttccgt cgcagccggg atttgggtcg cggttcttgt ttgt 164

<210> SEQ ID NO 15
<211> LENGTH: 225
<212> TYPE: DNA
<213> ORGANISM: Homo sapiens

<400> SEQUENCE: 15
caattgaggg cgtcaccgct aaggctccgc cccagcctgg gctccacaac caatgaaggg 60
taatctcgac aaagagcaag ggtggggcg cgggcgcgca ggtgcagcag cacacaggct 120
ggtcgggagg gcggggcgcg acgtctgccg tgcggggtcc cggcatcggt tgcgcgcgcg 180
ctccctcctc tcggagagag ggctgtggta aaacccgtcc ggaaa 225

<210> SEQ ID NO 16
<211> LENGTH: 123
<212> TYPE: DNA
<213> ORGANISM: Simian virus 40

<400> SEQUENCE: 16
tgtttattgc agcttataat ggttacaaat aaagcaatag catcacaaat ttcacaaata 60
aagcattttt ttcactgcat tctagttgtg gtttgtccaa actcatcaat gtatcttatc 120
atg 123

<210> SEQ ID NO 17
<211> LENGTH: 589
<212> TYPE: DNA
<213> ORGANISM: Artificial Sequence
<220> FEATURE:
<223> OTHER INFORMATION: pUC19 origin of replication

<400> SEQUENCE: 17
ttgagatcct ttttttctgc gcgtaatctg ctgcttgcaa acaaaaaaac caccgctacc 60

```
agcggtggtt tgtttgccgg atcaagagct accaactctt tttccgaagg taactggctt    120

cagcagagcg cagataccaa atactgttct tctagtgtag ccgtagttag gccaccactt    180

caagaactct gtagcaccgc ctacatacct cgctctgcta atcctgttac cagtggctgc    240

tgccagtggc gataagtcgt gtcttaccgg gttggactca agacgatagt taccggataa    300

ggcgcagcgg tcgggctgaa cggggggttc gtgcacacag cccagcttgg agcgaacgac    360

ctacaccgaa ctgagatacc tacagcgtga gctatgagaa agcgccacgc ttcccgaagg    420

gagaaaggcg gacaggtatc cggtaagcgg cagggtcgga acaggagagc gcacgaggga    480

gcttccaggg ggaaacgcct ggtatcttta tagtcctgtc gggtttcgcc acctctgact    540

tgagcgtcga tttttgtgat gctcgtcagg ggggcggagc ctatggaaa                589
```

<210> SEQ ID NO 18
<211> LENGTH: 816
<212> TYPE: DNA
<213> ORGANISM: Streptomyces kanamyceticus

<400> SEQUENCE: 18

```
atgagccata ttcaacggga aacgtcttgc tctaggccgc gattaaattc caacatggat     60

gctgatttat atgggtataa atgggctcgc gataatgtcg ggcaatcagg tgcgacaatc    120

tatcgattgt atgggaagcc cgatgcgcca gagttgtttc tgaaacatgg caaaggtagc    180

gttgccaatg atgttacaga tgagatggtc agactaaact ggctgacgga atttatgcct    240

cttccgacca tcaagcattt tatccgtact cctgatgatg catggttact caccactgcg    300

atccctggga aaacagcatt ccaggtatta gaagaatatc ctgattcagg tgaaaatatt    360

gttgatgcgc tggcagtgtt cctgcgccgg ttgcattcga ttcctgtttg taattgtcct    420

tttaacagcg atcgcgtatt tcgtctcgct caggcgcaat cacgaatgaa taacggtttg    480

gttgatgcga gtgattttga tgacgagcgt aatggctggc ctgttgaaca agtctggaaa    540

gaaatgcata aacttttgcc attctcaccg gattcagtcg tcactcatgg tgatttctca    600

cttgataacc ttatttttga cgaggggaaa ttaataggtt gtattgatgt tggacgagtc    660

ggaatcgcag accgatacca ggatcttgcc atcctatgga actgcctcgg tgagttttct    720

ccttcattac agaaacggct ttttcaaaaa tatggtattg ataatcctga tatgaataaa    780

ttgcagtttc atttgatgct cgatgagttt ttctaa                              816
```

<210> SEQ ID NO 19
<211> LENGTH: 105
<212> TYPE: DNA
<213> ORGANISM: Homo sapiens

<400> SEQUENCE: 19

```
cgcggaaccc ctatttgttt atttttctaa atacattcaa atatgtatcc gctcatgaga     60

caataaccct gataaatgct tcaataatat tgaaaaagga agagt                    105
```

<210> SEQ ID NO 20
<211> LENGTH: 2446
<212> TYPE: DNA
<213> ORGANISM: Artificial Sequence
<220> FEATURE:
<223> OTHER INFORMATION: rAAV vector

<400> SEQUENCE: 20

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggggtt cggtaccggg    120
```

-continued

```
cggagttagg gcggagccaa tcagcgtgcg ccgttccgaa agttgccttt tatggctggg    180
cggagaatgg gcggtgaacg ccgatgatta tataaggacg cgccgggtgt ggcacagcta    240
gttccgtcgc agccgggatt tgggtcgcgg ttcttgtttg ttccggaaag ccaccatggc    300
gaccaacggt agcaaggtcg cagacggcca gatcagcacc gaggtgtccg aagcccctgt    360
ggcgaacgat aagcccaaga ccctggtggt caaggtccag aagaaggcag cagacttgcc    420
ggatcgcgac acttggaagg gtcgcttcga cttcctgatg tcgtgcgtgg gctacgccat    480
tggactggga aacgtctgga ggttcccgta cctttgtggg aaaaatgggg gtggagcctt    540
tctgattccc tacttcctta ctctgatttt cgccggagtg cctctgtttc tactggagtg    600
cagcttgggg cagtacacgt ccatcggagg gctcggagtg tggaagctgg cgccgatgtt    660
caagggcgtg ggcttggctg ctgccgtgct gagcttctgg ctgaatatct actacatcgt    720
gatcatctcg tgggccatct actatcttta caactccttc accactactc tgccctggaa    780
acagtgcgac aacccctgga ataccgaccg gtgcttctct aactactcga tggtcaacac    840
cactaacatg accagcgccg tggtcgagtt ctgggagagg aacatgcatc aaatgacaga    900
cggcctcgac aagcccggac agattcggtg gccactggcc attaccctcg cgattgcatg    960
gatcttggtg tacttctgca tctggaaggg agtgggctgg actggaaagg tcgtgtactt   1020
ctcggccacc tacccgtaca ttatgctgat cattctgttt ttccggggcg tgactctgcc   1080
cggagccaag gaaggcatcc tgttctacat tactcctaac tttcggaagc tgtcggactc   1140
agaagtctgg ctggacgcag ctacccagat cttcttttcc tacggactgg gtctgggctc   1200
cctgatcgcc ctgggctcct ataactcctt ccacaacaac gtgtatcgcg actccatcat   1260
cgtgtgttgc atcaactcct gcacctcaat gttcgccggc ttcgtgatct tcagcattgt   1320
gggcttcatg gcccacgtga ccaagcgcag tatcgccgat gtggctgcgt ccggacctgg   1380
actggcgttc ctcgcgtacc cggaagccgt gacccagctc ccgatctcgc cgttgtgggc   1440
gattctcttc ttctccatgc ttctgatgct gggaatagac tcccagttct gtaccgtgga   1500
agggtttatc actgccctgg tggacgagta ccctagactg ctccggaacc ggagagaact   1560
gttcatcgct gccgtgtgca tcatttcata cctcatcggc ctcagcaaca tcacccaggg   1620
tggaatctac gtgttcaagc tgttcgacta ctattcggcc tccggaatgt ccctgctgtt   1680
cctggtgttc ttcgaatgcg tgtccatctc ctggttctac ggcgtcaacc ggttctacga   1740
taacattcag gaaatggtcg gatcacgccc ctgcatttgg tggaagctct gctggtcctt   1800
cttcaccccg atcatcgtgg ccggagtgtt catctttagc gctgtgcaga tgactcccct   1860
gactatgggg aactacgtgt tcccgaaatg ggtcaagga gtggggtggc tgatggcgct    1920
cagcagcatg gtgctgatcc ctggctacat ggcctacatg tttctgaccc tgaagggatc   1980
actgaagcag cgcatccaag tcatggtgca accctccgaa gatatcgtca gaccagaaaa   2040
cggacctgag cagccacagg ccggttcctc gacctccaaa gaggcctaca tctaataatg   2100
tacaagtaaa gcggccatca agctccggtt gatgaggagc tctcgagtgt ttattgcagc   2160
ttataatggt tacaaataaa gcaatagcat cacaaatttc acaaataaag catttttttc   2220
actgcattct agttgtggtt tgtccaaact catcaatgta tcttatcatg acgcgtagga   2280
acccctagtg atggagttgg ccactccctc tctgcgcgct cgctcgctca ctgaggccgg   2340
gcgaccaaag gtcgcccgac gcccgggctt tgcccgggcg gcctcagtga gcgagcgagc   2400
gcgccagctg gcgtaatagc gaagaggccc gcaccgatcg cccttc                  2446
```

<210> SEQ ID NO 21
<211> LENGTH: 6002
<212> TYPE: DNA
<213> ORGANISM: Artificial Sequence
<220> FEATURE:
<223> OTHER INFORMATION: plasmid comprising rAAV vector

<400> SEQUENCE: 21
ctgcgcgctc gctcgctcac tgaggccgcc cgggcaaagc ccgggcgtcg ggcgaccttt 60
ggtcgcccgg cctcagtgag cgagcgagcg cgcagagagg gagtggggtt cggtaccggg 120
cggagttagg gcggagccaa tcagcgtgcg ccgttccgaa agttgccttt tatggctggg 180
cggagaatgg gcggtgaacg ccgatgatta tataaggacg cgccgggtgt ggcacagcta 240
gttccgtcgc agccgggatt tgggtcgcgg ttcttgtttg ttccggaaag ccaccatggc 300
gaccaacggt agcaaggtcg cagacggcca gatcagcacc gaggtgtccg aagcccctgt 360
ggcgaacgat aagcccaaga ccctggtggt caaggtccag aagaaggcag cagacttgcc 420
ggatcgcgac acttggaagg gtcgcttcga cttcctgatg tcgtgcgtgg gctacgccat 480
tggactggga aacgtctgga ggttcccgta cctttgtggg aaaaatgggg gtggagcctt 540
tctgattccc tacttcctta ctctgatttt cgccggagtg cctctgtttc tactggagtg 600
cagcttgggg cagtacacgt ccatcggagg gctcggagtg tggaagctgg cgccgatgtt 660
caagggcgtg ggcttggctg ctgccgtgct gagcttctgg ctgaatatct actacatcgt 720
gatcatctcg tgggccatct actatcttta caactccttc accactactc tgccctggaa 780
acagtgcgac aacccctgga ataccgaccg gtgcttctct aactactcga tggtcaacac 840
cactaacatg accagcgccg tggtcgagtt ctgggagagg aacatgcatc aaatgacaga 900
cggcctcgac aagcccggac agattcggtg gccactggcc attaccctcg cgattgcatg 960
gatcttggtg tacttctgca tctggaaggg agtgggctgg actggaaagg tcgtgtactt 1020
ctcggccacc tacccgtaca ttatgctgat cattctgttt ttccggggcg tgactctgcc 1080
cggagccaag gaaggcatcc tgttctacat tactcctaac tttcggaagc tgtcggactc 1140
agaagtctgg ctggacgcag ctacccagat cttcttttcc tacggactgg gtctgggctc 1200
cctgatcgcc ctgggctcct ataactcctt ccacaacaac gtgtatcgcg actccatcat 1260
cgtgtgttgc atcaactcct gcacctcaat gttcgccggc ttcgtgatct tcagcattgt 1320
gggcttcatg gcccacgtga ccaagcgcag tatcgccgat gtggctgcgt ccggacctgg 1380
actggcgttc ctcgcgtacc cggaagccgt gacccagctc ccgatctcgc cgttgtgggc 1440
gattctcttc ttctccatgc ttctgatgct gggaatagac tcccagttct gtaccgtgga 1500
agggtttatc actgccctgg tggacgagta ccctagactg ctccggaacc ggagagaact 1560
gttcatcgct gccgtgtgca tcatttcata cctcatcggc ctcagcaaca tcacccaggg 1620
tggaatctac gtgttcaagc tgttcgacta ctattcggcc tccggaatgt ccctgctgtt 1680
cctggtgttc ttcgaatgcg tgtccatctc ctggttctac ggcgtcaacc ggttctacga 1740
taacattcag gaaatggtcg gatcacgccc ctgcatttgg tggaagctct gctggtcctt 1800
cttcaccccg atcatcgtgg ccggagtgtt catctttagc gctgtgcaga tgactcccct 1860
gactatgggg aactacgtgt tcccgaaatg ggggtcaagga gtggggtggc tgatggcgct 1920
cagcagcatg gtgctgatcc ctggctacat ggcctacatg tttctgaccc tgaagggatc 1980
actgaagcag cgcatccaag tcatggtgca accctccgaa gatatcgtca gaccagaaaa 2040
cggacctgag cagccacagg ccggttcctc gacctccaaa gaggcctaca tctaataatg 2100

```
tacaagtaaa gcggccatca agctccggtt gatgaggagc tctcgagtgt ttattgcagc   2160
ttataatggt tacaaataaa gcaatagcat cacaaatttc acaaataaag cattttttc    2220
actgcattct agttgtggtt tgtccaaact catcaatgta tcttatcatg acgcgtagga   2280
acccctagtg atggagttgg ccactccctc tctgcgcgct cgctcgctca ctgaggccgg   2340
gcgaccaaag gtcgcccgac gcccgggctt tgcccgggcg gcctcagtga gcgagcgagc   2400
gcgccagctg gcgtaatagc gaagaggccc gcaccgatcg cccttcccaa cagttgcgca   2460
gcctgaatgg cgaatggaat tccagacgat tgagcgtcaa aatgtaggta tttccatgag   2520
cgtttttcct gttgcaatgg ctggcggtaa tattgttctg gatattacca gcaaggccga   2580
tagtttgagt tcttctactc aggcaagtga tgttattact aatcaaagaa gtattgcgac   2640
aacggttaat ttgcgtgatg gacagactct tttactcggt ggcctcactg attataaaaa   2700
cacttctcag gattctggcg taccgttcct gtctaaaatc cctttaatcg gcctcctgtt   2760
tagctcccgc tctgattcta acgaggaaag cacgttatac gtgctcgtca aagcaaccat   2820
agtacgcgcc ctgtagcggc gcattaagcg cggcgggtgt ggtggttacg cgcagcgtga   2880
ccgctacact tgccagcgcc ctagcgcccg ctcctttcgc tttcttccct tcctttctcg   2940
ccacgttcgc cggctttccc cgtcaagctc taaatcgggg gctcccttta gggttccgat   3000
ttagtgcttt acggcacctc gaccccaaaa aacttgatta gggtgatggt tcacgtagtg   3060
ggccatcgcc ctgatagacg gtttttcgcc ctttgacgtt ggagtccacg ttctttaata   3120
gtggactctt gttccaaact ggaacaacac tcaaccctat ctcggtctat tcttttgatt   3180
tataagggat tttgccgatt tcggcctatt ggttaaaaaa tgagctgatt taacaaaaat   3240
ttaacgcgaa ttttaacaaa atattaacgc ttacaattta aatatttgct tatacaatct   3300
tcctgttttt ggggcttttc tgattatcaa ccggggtaca tatgattgac atgctagttt   3360
tacgattacc gttcatcgat tctcttgttt gctccagact ctcaggcaat gacctgatag   3420
cctttgtaga gacctctcaa aaatagctac cctctccggc atgaatttat cagctagaac   3480
ggttgaatat catattgatg gtgatttgac tgtctccggc ctttctcacc cgtttgaatc   3540
tttacctaca cattactcag gcattgcatt taaaatatat gagggttcta aaaattttta   3600
tccttgcgtt gaaataaagg cttctcccgc aaaagtatta cagggtcata atgtttttgg   3660
tacaaccgat ttagctttat gctctgaggc tttattgctt aattttgcta attctttgcc   3720
ttgcctgtat gatttattgg atgttggaat cgcctgatgc ggtattttct ccttacgcat   3780
ctgtgcggta tttcacaccg catatggtgc actctcagta caatctgctc tgatgccgca   3840
tagttaagcc agccccgaca cccgccaaca cccgctgacg cgccctgacg ggcttgtctg   3900
ctcccggcat ccgcttacag acaagctgtg accgtctccg ggagctgcat gtgtcagagg   3960
ttttcaccgt catcaccgaa acgcgcgaga cgaaagggcc tcgtgatacg cctattttta   4020
taggttaatg tcatgataat aatggtttct tagacgtcag gtggcacttt tcggggaaat   4080
gtgcgcggaa cccctatttg tttatttttc taaatacatt caaatatgta tccgctcatg   4140
agacaataac cctgataaat gcttcaataa tattgaaaaa ggaagagtat gagccatatt   4200
caacgggaaa cgtcttgctc taggccgcga ttaaattcca acatggatgc tgatttatat   4260
gggtataaat gggctcgcga taatgtcggg caatcaggtg cgacaatcta tcgattgtat   4320
gggaagcccg atgcgccaga gttgtttctg aaacatggca aaggtagcgt tgccaatgat   4380
gttacagatg agatggtcag actaaactgg ctgacggaat ttatgcctct tccgaccatc   4440
```

aagcatttta tccgtactcc tgatgatgca tggttactca ccactgcgat ccctgggaaa 4500
acagcattcc aggtattaga agaatatcct gattcaggtg aaaatattgt tgatgcgctg 4560
gcagtgttcc tgcgccggtt gcattcgatt cctgtttgta attgtccttt taacagcgat 4620
cgcgtatttc gtctcgctca ggcgcaatca cgaatgaata acggtttggt tgatgcgagt 4680
gattttgatg acgagcgtaa tggctggcct gttgaacaag tctggaaaga aatgcataaa 4740
cttttgccat tctcaccgga ttcagtcgtc actcatggtg atttctcact tgataacctt 4800
atttttgacg aggggaaatt aataggttgt attgatgttg gacgagtcgg aatcgcagac 4860
cgataccagg atcttgccat cctatggaac tgcctcggtg agttttctcc ttcattacag 4920
aaacggcttt ttcaaaaata tggtattgat aatcctgata tgaataaatt gcagtttcat 4980
ttgatgctcg atgagttttt ctaactgtca gaccaagttt actcatatat actttagatt 5040
gatttaaaac ttcattttta atttaaaagg atctaggtga agatcctttt tgataatctc 5100
atgaccaaaa tcccttaacg tgagttttcg ttccactgag cgtcagaccc cgtagaaaag 5160
atcaaaggat cttcttgaga tcctttttt ctgcgcgtaa tctgctgctt gcaaacaaaa 5220
aaaccaccgc taccagcggt ggtttgtttg ccggatcaag agctaccaac tctttttccg 5280
aaggtaactg gcttcagcag agcgcagata ccaaatactg ttcttctagt gtagccgtag 5340
ttaggccacc acttcaagaa ctctgtagca ccgcctacat acctcgctct gctaatcctg 5400
ttaccagtgg ctgctgccag tggcgataag tcgtgtctta ccgggttgga ctcaagacga 5460
tagttaccgg ataaggcgca gcggtcgggc tgaacggggg gttcgtgcac acagcccagc 5520
ttggagcgaa cgacctacac cgaactgaga tacctacagc gtgagctatg agaaagcgcc 5580
acgcttcccg aagggagaaa ggcggacagg tatccggtaa gcggcagggt cggaacagga 5640
gagcgcacga gggagcttcc agggggaaac gcctggtatc tttatagtcc tgtcgggttt 5700
cgccacctct gacttgagcg tcgatttttg tgatgctcgt caggggggcg gagcctatgg 5760
aaaaacgcca gcaacgcggc ctttttacgg ttcctggcct tttgctggcc ttttgctcac 5820
atgttctttc ctgcgttatc ccctgattct gtggataacc gtattaccgc ctttgagtga 5880
gctgataccg ctcgccgcag ccgaacgacc gagcgcagcg agtcagtgag cgaggaagcg 5940
gaagagcgcc caatacgcaa accgcctctc cccgcgcgtt ggccgattca ttaatgcagc 6000
ag 6002

<210> SEQ ID NO 22
<211> LENGTH: 2499
<212> TYPE: DNA
<213> ORGANISM: Artificial Sequence
<220> FEATURE:
<223> OTHER INFORMATION: rAAV vector

<400> SEQUENCE: 22
ctgcgcgctc gctcgctcac tgaggccgcc cgggcaaagc ccgggcgtcg ggcgaccttt 60
ggtcgcccgg cctcagtgag cgagcgagcg cgcagagagg gagtggggtt cggtacccaa 120
ttgagggcgt caccgctaag gctccgcccc agcctgggct ccacaaccaa tgaagggtaa 180
tctcgacaaa gagcaagggg tggggcgcgg gcgcgcaggt gcagcagcac acaggctggt 240
cgggagggcg gggcgcgacg tctgccgtgc ggggtcccgg catcggttgc gcgcgcgctc 300
cctcctctcg gagagagggc tgtggtaaaa cccgtccgga aagccaccat ggcgaccaac 360
ggtagcaagg tcgcagacgg ccagatcagc accgaggtgt ccgaagcccc tgtggcgaac 420
gataagccca agaccctggt ggtcaaggtc cagaagaagg cagcagactt gccggatcgc 480

```
gacacttgga agggtcgctt cgacttcctg atgtcgtgcg tgggctacgc cattggactg    540
ggaaacgtct ggaggttccc gtacctttgt gggaaaaatg ggggtggagc ctttctgatt    600
ccctacttcc ttactctgat tttcgccgga gtgcctctgt ttctactgga gtgcagcttg    660
gggcagtaca cgtccatcgg agggctcgga gtgtggaagc tggcgccgat gttcaagggc    720
gtgggcttgg ctgctgccgt gctgagcttc tggctgaata tctactacat cgtgatcatc    780
tcgtgggcca tctactatct ttacaactcc ttcaccacta ctctgccctg gaaacagtgc    840
gacaacccct ggaataccga ccggtgcttc tctaactact cgatggtcaa caccactaac    900
atgaccagcg ccgtggtcga gttctgggag aggaacatgc atcaaatgac agacggcctc    960
gacaagcccg gacagattcg gtggccactg gccattaccc tcgcgattgc atggatcttg   1020
gtgtacttct gcatctggaa gggagtgggc tggactggaa aggtcgtgta cttctcggcc   1080
acctacccgt acattatgct gatcattctg tttttccggg gcgtgactct gcccggagcc   1140
aaggaaggca tcctgttcta cattactcct aactttcgga agctgtcgga ctcagaagtc   1200
tggctggacg cagctaccca gatcttcttt tcctacggac tgggtctggg ctccctgatc   1260
gccctgggct cctataactc cttccacaac aacgtgtatc gcgactccat catcgtgtgt   1320
tgcatcaact cctgcacctc aatgttcgcc ggcttcgtga tcttcagcat tgtgggcttc   1380
atggcccacg tgaccaagcg cagtatcgcc gatgtggctg cgtccggacc tggactggcg   1440
ttcctcgcgt acccggaagc cgtgacccag ctcccgatct cgccgttgtg ggcgattctc   1500
ttcttctcca tgcttctgat gctgggaata gactcccagt tctgtaccgt ggaagggttt   1560
atcactgccc tggtggacga gtaccctaga ctgctccgga accggagaga actgttcatc   1620
gctgccgtgt gcatcatttc atacctcatc ggcctcagca acatcaccca gggtggaatc   1680
tacgtgttca agctgttcga ctactattcg gcctccggaa tgtccctgct gttcctggtg   1740
ttcttcgaat gcgtgtccat ctcctggttc tacggcgtca accggttcta cgataacatt   1800
caggaaatgg tcggatcacg cccctgcatt tggtggaagc tctgctggtc cttcttcacc   1860
ccgatcatcg tggccggagt gttcatcttt agcgctgtgc agatgactcc cctgactatg   1920
gggaactacg tgttcccgaa atggggtcaa ggagtggggt ggctgatggc gctcagcagc   1980
atggtgctga tccctggcta catggcctac atgtttctga ccctgaaggg atcactgaag   2040
cagcgcatcc aagtcatggt gcaaccctcc gaagatatcg tcagaccaga aaacggacct   2100
gagcagccac aggccggttc ctcgacctcc aaagaggcct acatctaata atgtacaagt   2160
aaagcggcca tcaagctccg gttgatgagg agctctcgag tgtttattgc agcttataat   2220
ggttacaaat aaagcaatag catcacaaat ttcacaaata aagcattttt ttcactgcat   2280
tctagttgtg gtttgtccaa actcatcaat gtatcttatc atgacgcgta ggaacccta    2340
gtgatggagt tggccactcc ctctctgcgc gctcgctcgc tcactgaggc cgggcgacca   2400
aaggtcgccc gacgcccggg ctttgcccgg gcggcctcag tgagcgagcg agcgcgccag   2460
ctggcgtaat agcgaagagg cccgcaccga tcgcccttc                          2499
```

<210> SEQ ID NO 23
<211> LENGTH: 6055
<212> TYPE: DNA
<213> ORGANISM: Artificial Sequence
<220> FEATURE:
<223> OTHER INFORMATION: full MeP229 construct

<400> SEQUENCE: 23

-continued

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggggtt cggtacccaa    120
ttgagggcgt caccgctaag gctccgcccc agcctgggct ccacaaccaa tgaagggtaa    180
tctcgacaaa gagcaagggg tggggcgcgg gcgcgcaggt gcagcagcac acaggctggt    240
cgggagggcg gggcgcgacg tctgccgtgc ggggtcccgg catcggttgc gcgcgcgctc    300
cctcctctcg gagagagggc tgtggtaaaa cccgtccgga aagccaccat ggcgaccaac    360
ggtagcaagg tcgcagacgg ccagatcagc accgaggtgt ccgaagcccc tgtggcgaac    420
gataagccca agaccctggt ggtcaaggtc cagaagaagg cagcagactt gccggatcgc    480
gacacttgga agggtcgctt cgacttcctg atgtcgtgcg tgggctacgc cattggactg    540
ggaaacgtct ggaggttccc gtacctttgt gggaaaaatg gggggtggagc ctttctgatt   600
ccctacttcc ttactctgat ttcgccgga gtgcctctgt ttctactgga gtgcagcttg     660
gggcagtaca cgtccatcgg agggctcgga gtgtggaagc tggcgccgat gttcaagggc    720
gtgggcttgg ctgctgccgt gctgagcttc tggctgaata tctactacat cgtgatcatc    780
tcgtgggcca tctactatct ttacaactcc ttcaccacta ctctgccctg gaaacagtgc    840
gacaacccct ggaataccga ccggtgcttc tctaactact cgatggtcaa caccactaac    900
atgaccagcg ccgtggtcga gttctgggag aggaacatgc atcaaatgac agacggcctc    960
gacaagcccg gacagattcg gtggccactg gccattaccc tcgcgattgc atggatcttg   1020
gtgtacttct gcatctggaa gggagtgggc tggactggaa aggtcgtgta cttctcggcc   1080
acctacccgt acattatgct gatcattctg tttttccggg gcgtgactct gcccggagcc   1140
aaggaaggca tcctgttcta cattactcct aactttcgga agctgtcgga ctcagaagtc   1200
tggctggacg cagctaccca gatcttcttt tcctacggac tgggtctggg ctccctgatc   1260
gccctgggct cctataactc cttccacaac aacgtgtatc gcgactccat catcgtgtgt   1320
tgcatcaact cctgcacctc aatgttcgcc ggcttcgtga tcttcagcat tgtgggcttc   1380
atggcccacg tgaccaagcg cagtatcgcc gatgtggctg cgtccggacc tggactggcg   1440
ttcctcgcgt acccggaagc cgtgacccag ctcccgatct cgccgttgtg ggcgattctc   1500
ttcttctcca tgcttctgat gctgggaata gactcccagt tctgtaccgt ggaagggttt   1560
atcactgccc tggtggacga gtaccctaga ctgctccgga accggagaga actgttcatc   1620
gctgccgtgt gcatcatttc atacctcatc ggcctcagca acatcaccca gggtggaatc   1680
tacgtgttca agctgttcga ctactattcg gcctccggaa tgtccctgct gttcctggtg   1740
ttcttcgaat gcgtgtccat ctcctggttc tacggcgtca accggttcta cgataacatt   1800
caggaaatgg tcggatcacg cccctgcatt tggtggaagc tctgctggtc cttcttcacc   1860
ccgatcatcg tggccggagt gttcatcttt agcgctgtgc agatgactcc cctgactatg   1920
gggaactacg tgttcccgaa atggggtcaa ggagtggggt ggctgatggc gctcagcagc   1980
atggtgctga tccctggcta catggcctac atgtttctga ccctgaaggg atcactgaag   2040
cagcgcatcc aagtcatggt gcaaccctcc gaagatatcg tcagaccaga aaacggacct   2100
gagcagccac aggccggttc ctcgacctcc aaagaggcct acatctaata atgtacaagt   2160
aaagcggcca tcaagctccg gttgatgagg agctctcgag tgtttattgc agcttataat   2220
ggttacaaat aaagcaatag catcacaaat ttcacaaata aagcattttt ttcactgcat   2280
tctagttgtg gtttgtccaa actcatcaat gtatcttatc atgacgcgta ggaaccccta   2340
gtgatggagt tggccactcc ctctctgcgc gctcgctcgc tcactgaggc cgggcgacca   2400
```

-continued

```
aaggtcgccc gacgcccggg ctttgcccgg gcggcctcag tgagcgagcg agcgcgccag   2460
ctggcgtaat agcgaagagg cccgcaccga tcgcccttcc caacagttgc gcagcctgaa   2520
tggcgaatgg aattccagac gattgagcgt caaaatgtag gtatttccat gagcgttttt   2580
cctgttgcaa tggctggcgg taatattgtt ctggatatta ccagcaaggc cgatagtttg   2640
agttcttcta ctcaggcaag tgatgttatt actaatcaaa gaagtattgc gacaacggtt   2700
aatttgcgtg atggacagac tcttttactc ggtggcctca ctgattataa aaacacttct   2760
caggattctg gcgtaccgtt cctgtctaaa atccctttaa tcggcctcct gtttagctcc   2820
cgctctgatt ctaacgagga aagcacgtta tacgtgctcg tcaaagcaac catagtacgc   2880
gccctgtagc ggcgcattaa gcgcggcggg tgtggtggtt acgcgcagcg tgaccgctac   2940
acttgccagc gccctagcgc ccgctccttt cgctttcttc ccttcctttc tcgccacgtt   3000
cgccggcttt ccccgtcaag ctctaaatcg ggggctccct ttagggttcc gatttagtgc   3060
tttacggcac ctcgacccca aaaaacttga ttagggtgat ggttcacgta gtgggccatc   3120
gccctgatag acggtttttc gccctttgac gttggagtcc acgttcttta atagtggact   3180
cttgttccaa actggaacaa cactcaaccc tatctcggtc tattcttttg atttataagg   3240
gattttgccg atttcggcct attggttaaa aaatgagctg atttaacaaa aatttaacgc   3300
gaattttaac aaaatattaa cgcttacaat ttaaatattt gcttatacaa tcttcctgtt   3360
tttggggctt ttctgattat caaccggggt acatatgatt gacatgctag ttttacgatt   3420
accgttcatc gattctcttg tttgctccag actctcaggc aatgacctga tagcctttgt   3480
agagacctct caaaaatagc taccctctcc ggcatgaatt tatcagctag aacggttgaa   3540
tatcatattg atggtgattt gactgtctcc ggcctttctc acccgtttga atctttacct   3600
acacattact caggcattgc atttaaaata tatgagggtt ctaaaaattt ttatccttgc   3660
gttgaaataa aggcttctcc cgcaaaagta ttacagggtc ataatgtttt tggtacaacc   3720
gatttagctt tatgctctga ggctttattg cttaattttg ctaattcttt gccttgcctg   3780
tatgatttat tggatgttgg aatcgcctga tgcggtattt tctccttacg catctgtgcg   3840
gtatttcaca ccgcatatgg tgcactctca gtacaatctg ctctgatgcc gcatagttaa   3900
gccagccccg acacccgcca acacccgctg acgcgccctg acgggcttgt ctgctcccgg   3960
catccgctta cagacaagct gtgaccgtct ccgggagctg catgtgtcag aggttttcac   4020
cgtcatcacc gaaacgcgcg agacgaaagg gcctcgtgat acgcctattt ttataggtta   4080
atgtcatgat aataatggtt tcttagacgt caggtggcac ttttcgggga aatgtgcgcg   4140
gaacccctat ttgtttattt ttctaaatac attcaaatat gtatccgctc atgagacaat   4200
aaccctgata aatgcttcaa taatattgaa aaaggaagag tatgagccat attcaacggg   4260
aaacgtcttg ctctaggccg cgattaaatt ccaacatgga tgctgattta tatgggtata   4320
aatgggctcg cgataatgtc gggcaatcag gtgcgacaat ctatcgattg tatgggaagc   4380
ccgatgcgcc agagttgttt ctgaaacatg gcaaaggtag cgttgccaat gatgttacag   4440
atgagatggt cagactaaac tggctgacgg aatttatgcc tcttccgacc atcaagcatt   4500
ttatccgtac tcctgatgat gcatggttac tcaccactgc gatccctggg aaaacagcat   4560
tccaggtatt agaagaatat cctgattcag gtgaaaatat tgttgatgcg ctggcagtgt   4620
tcctgcgccg gttgcattcg attcctgttt gtaattgtcc ttttaacagc gatcgcgtat   4680
ttcgtctcgc tcaggcgcaa tcacgaatga ataacggttt ggttgatgcg agtgattttg   4740
```

atgacgagcg taatggctgg cctgttgaac aagtctggaa agaaatgcat aaacttttgc 4800
cattctcacc ggattcagtc gtcactcatg gtgatttctc acttgataac cttatttttg 4860
acgaggggaa attaataggt tgtattgatg ttggacgagt cggaatcgca gaccgatacc 4920
aggatcttgc catcctatgg aactgcctcg gtgagttttc tccttcatta cagaaacggc 4980
tttttcaaaa atatggtatt gataatcctg atatgaataa attgcagttt catttgatgc 5040
tcgatgagtt tttctaactg tcagaccaag tttactcata tatactttag attgatttaa 5100
aacttcattt ttaatttaaa aggatctagg tgaagatcct ttttgataat ctcatgacca 5160
aaatccctta acgtgagttt tcgttccact gagcgtcaga ccccgtagaa aagatcaaag 5220
gatcttcttg agatcctttt tttctgcgcg taatctgctg cttgcaaaca aaaaaaccac 5280
cgctaccagc ggtggtttgt ttgccggatc aagagctacc aactcttttt ccgaaggtaa 5340
ctggcttcag cagagcgcag ataccaaata ctgttcttct agtgtagccg tagttaggcc 5400
accacttcaa gaactctgta gcaccgccta catacctcgc tctgctaatc ctgttaccag 5460
tggctgctgc cagtggcgat aagtcgtgtc ttaccgggtt ggactcaaga cgatagttac 5520
cggataaggc gcagcggtcg ggctgaacgg ggggttcgtg cacacagccc agcttggagc 5580
gaacgaccta caccgaactg agatacctac agcgtgagct atgagaaagc gccacgcttc 5640
ccgaagggag aaaggcggac aggtatccgg taagcggcag ggtcggaaca ggagagcgca 5700
cgagggagct tccaggggga aacgcctggt atctttatag tcctgtcggg tttcgccacc 5760
tctgacttga gcgtcgattt ttgtgatgct cgtcaggggg gcggagccta tggaaaaacg 5820
ccagcaacgc ggccttttta cggttcctgg ccttttgctg gccttttgct cacatgttct 5880
ttcctgcgtt atcccctgat tctgtggata accgtattac cgcctttgag tgagctgata 5940
ccgctcgccg cagccgaacg accgagcgca gcgagtcagt gagcgaggaa gcggaagagc 6000
gcccaatacg caaaccgcct ctccccgcgc gttggccgat tcattaatgc agcag 6055

<210> SEQ ID NO 24
<211> LENGTH: 796
<212> TYPE: DNA
<213> ORGANISM: Artificial Sequence
<220> FEATURE:
<223> OTHER INFORMATION: cBh promoter

<400> SEQUENCE: 24
tacataactt acggtaaatg gcccgcctgg ctgaccgccc aacgaccccc gcccattgac 60
gtcaatagta acgccaatag ggactttcca ttgacgtcaa tgggtggagt atttacggta 120
aactgcccac ttggcagtac atcaagtgta tcatatgcca agtacgcccc ctattgacgt 180
caatgacggt aaatggcccg cctggcattg tgcccagtac atgaccttat gggactttcc 240
tacttggcag tacatctacg tattagtcat cgctattacc atggtcgagg tgagccccac 300
gttctgcttc actctcccca tctccccccc ctccccaccc ccaattttgt atttatttat 360
tttttaatta ttttgtgcag cgatgggggc gggggggggg ggggggcgcg cgccaggcgg 420
ggcggggcgg ggcgaggggc ggggcggggc gaggcggaga ggtgcggcgg cagccaatca 480
gagcggcgcg ctccgaaagt ttccttttat ggcgaggcgg cggcggcggc ggccctataa 540
aaagcgaagc gcgcggcggg cgggagtcgc tgcgacgctg ccttcgcccc gtgccccgct 600
ccgccgccgc ctcgcgccgc ccgccccggc tctgactgac cgcgttactc ccacaggtga 660

-continued

```
gcgggcggga cggcccttct cctccgggct gtaattagct gagcaagagg taagggttta    720

agggatggtt ggttggtggg gtattaatgt ttaattacct ggagcacctg cctgaaatca    780

cttttttca ggttgg                                                     796
```